United States Patent [19]

Angerbauer et al.

[11] Patent Number: 4,757,065
[45] Date of Patent: Jul. 12, 1988

[54] CEPHALOSPORINS

[75] Inventors: Rolf Angerbauer; Michael Boberg; Karl G. Metzger, all of Wuppertal; Hans-Joachim Zeiler, Velbert, all of Fed. Rep. of Germany

[73] Assignee: Bayer Aktiengesellschaft, Leverkusen, Fed. Rep. of Germany

[21] Appl. No.: 673,246

[22] Filed: Nov. 20, 1984

[30] Foreign Application Priority Data

Nov. 30, 1983 [DE] Fed. Rep. of Germany ....... 3343208

[51] Int. Cl.$^4$ ................. C07D 501/38; A61K 31/545
[52] U.S. Cl. .................................. 514/203; 514/202; 540/225; 540/222
[58] Field of Search ................... 544/25, 24; 424/246; 540/225, 222; 514/202, 203

[56] References Cited

U.S. PATENT DOCUMENTS 4,416,880 11/1983 Boberg et al. ...................... 540/225
4,489,076 12/1984 Kinast et al. ........................ 424/246

FOREIGN PATENT DOCUMENTS 0049448 4/1982 European Pat. Off. .
0081674 6/1983 European Pat. Off. .
0107138 5/1984 European Pat. Off. .
2076801A 12/1981 United Kingdom .

Primary Examiner—Nicholas S. Rizzo
Attorney, Agent, or Firm—Sprung Horn Kramer & Woods

[57] ABSTRACT

Antibacterially effective cephalosporins of the formula

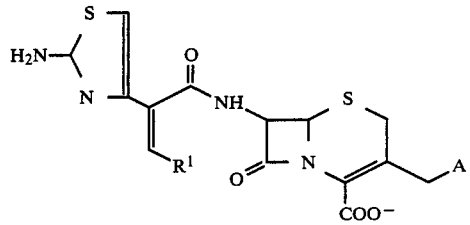

in which
$R^1$ denotes $C_1$–$C_6$-alkyl, phenyl or halogen-substituted phenyl and
A represents a nitrogen-containing, positively charged heterocyclic 5-membered to 7-membered ring which is bonded via N and can contain a total of up to 4 hetero-atoms from the group comprising N, O and S, and onto which up to two further rings can be fused, and which can optionally be substituted, with the proviso that, if the ring is a 6-membered ring, A does not represent an unsubstituted pyridine ring or a pyridine ring which is mono- or di-substituted by identical or different substituents from the group comprising $C_1$–$C_4$-alkyl, chlorine, bromine, carbamoyl or N—$C_1$–$C_4$-alkylcarbamoyl,
or pharmaceutically acceptable salts thereof or esters thereof which can be split under physiological conditions.

11 Claims, No Drawings

CEPHALOSPORINS

The invention relates to new cephalosporins, their use as medicaments, in particular in antibacterial therapy, and processes for their preparation.

Cephalosporins which carry an aminothiazolylacrylic acid radical as an acyl side chain are known from European Pat. A-49,448.

The present invention provides cephalosporins of the general formula I, pharmaceutically acceptable salts thereof and esters thereof which can be split under physiological conditions,

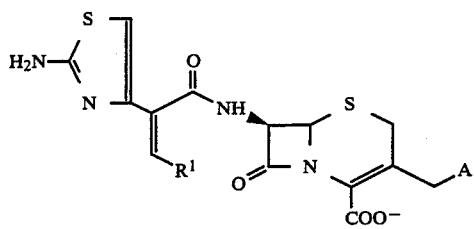     (I)

in which
$R^1$ denotes $C_1$–$C_6$-alkyl, phenyl or halogen-substituted phenyl and A represents a nitrogen-containing, positively charged heterocyclic 5-membered to 7-membered ring which is bonded via N and can contain a total of up to 4 hetero-atoms from the group comprising N, O and S, and onto which up to two further rings can be fused, and which can optionally be substituted, with the proviso that, if the ring is a 6-membered ring, A does not represent an unsubstituted pyridine ring or a pyridine ring which is mono- or di-substituted by identical or different substituents from the group comprising $C_1$–$C_4$-alkyl, chlorine, bromine, carbamoyl or N—$C_1$–$C_4$-alkylcarbamoyl.

Preferred compounds are those in which A denotes a nitrogen-containing, positively charged 6-membered ring which is bonded via N and contains a total of up to 3 nitrogen atoms, and onto which up to two further rings can be fused, and which can optionally be substituted, but does not denote an unsubstituted pyridine ring or a pyridine ring which is mono- or di-substituted by identical or different substituents from the group comprising $C_1$–$C_4$-alkyl, chlorine, bromine, carbamoyl and N—$C_1$–$C_4$-alkylcarbamoyl.

Compounds which are furthermore preferred are those in which
$R_1$ has the abovementioned meaning and
A denotes a pyridinium radical

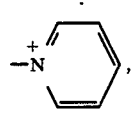, which is mono- or polysubstituted, preferably mono-, di- or tri-substituted, by identical or different substituents as follows: by substituted $C_1$–$C_6$-alkyl, by cyano-$C_1$–$C_3$-alkyl, epoxy-$C_2$–$C_6$-alkyl, trifluoromethyl or pentafluoroethyl, by hydroximino-methyl or $C_1$–$C_4$-alkoximinomethyl, by optionally substituted $C_2$–$C_6$-alkenyl, by $C_2$–$C_6$-alkinyl, by $C_3$–$C_7$-cycloalkyl or $C_3$–$C_7$-cycloalkyl-methyl, it being possible for the ring in both substituents also to be substituted, by $C_4$–$C_7$-cycloalkenyl, by optionally substituted $C_1$–$C_6$-alkoxy, by epoxy-$C_2$–$C_6$-alkoxy, by $C_2$–$C_6$-alkenyloxy or $C_2$–$C_6$-alkinyloxy, by optionally substituted phenoxy or heteroaryloxy, by amino, which can optionally be mono- or di-substituted, by cyano, hydroxyl or mercapto, by $C_1$–$C_6$-alkylthio, $C_1$–$C_6$-alkylsulphinyl or $C_1$–$C_6$-alkylsulphonyl, each of which is optionally substituted in the alkyl part, by methylthio, methylsulphinyl or methylsulphonyl, each of which is substituted on the methyl radical, by $C_2$–$C_6$-alkenylthio, $C_2$–$C_6$-alkenylsulphinyl or $C_2$–$C_6$-alkenylsulphonyl, by optionally substituted phenyl, benzyl or heteroaryl, by formyl or ketalized formyl, by optionally substituted $C_1$–$C_6$-alkylcarbonyl, which can also be in ketalized form, by arylcarbonyl, by $C_1$–$C_6$-alkylcarbonylamino, by carboxyl or $C_1$–$C_6$-alkoxycarbonyl, and by sulphamoyl, which can be monosubstituted on the nitrogen, and onto which one or two optionally substituted 3-membered to 7-membered rings can be fused, each of which can contain up to two heteroatoms and up to two double bonds and can also be aromatic or heteroaromatic.

The present invention particularly relates to compounds in which
$R_1$ has the above meaning and
A denotes a pyridinium radical

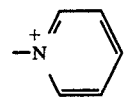

which is mono- or polysubstituted, preferably mono-, di- or tri-substituted, by identical or different substituents as follows: by $C_1$–$C_6$-alkyl, which is monosubstituted or polysubstituted, by hydroxyl, carboxyl, $C_1$–$C_6$-alkoxycarbonyl, formyl or $C_1$–$C_6$-alkylcarbonyl, the carbonyl groups of which can also be in ketalized form, carbamoyl, N-hydroxy-carbamoyl, sulpho, $C_1$–$C_6$-alkoxy, hydroxy-$C_1$–$C_6$-alkoxy, $C_1$–$C_6$alkylthio, $C_1$–$C_6$-alkylsulphinyl, $C_1$–$C_6$-alkylsulphonyl, $C_2$–$C_6$-alkenyloxy, $C_2$–$C_6$-alkenylthio, $C_2$–$C_6$-alkenylsulphinyl or $C_2$–$C_6$-alkenylsulphonyl, by cyano-$C_1$–$C_3$-alkyl, epoxy-$C_2$–$C_6$-alkyl, hydroxyiminomethyl, $C_1$–$C_4$-alkoxyiminomethyl, trifluoromethyl or pentafluoroethyl by $C_2$–$C_6$-alkenyl, which can be substituted by hydroxyl, by $C_2$–$C_6$-alkinyl, by $C_3$–$C_7$-cycloalkyl or $C_3$–$C_7$-cycloalkylmethyl, it being possible for the ring in both substituents also to be substituted by hydroxyl, halogen, carboxyl, $C_1$–$C_6$-alkoxycarbonyl or cyano, by $C_4$–$C_7$-cycloalkenyl, by $C_1$–$C_6$-alkoxy, which can be substituted by hydroxyl, carboxyl or $C_1$–$C_6$-alkoxycarbonyl, by epoxy-$C_2$–$C_6$-alkoxy, by $C_2$–$C_6$-alkenyloxy or $C_2$–$C_6$-alkinyloxy, by optionally substituted phenoxy or heteroaryloxy, by amino, which can be mono- or di-substituted by identical or different substituents from the group comprising $C_1$–$C_6$alkyl, formyl, $C_1$–$C_6$-alkylcarbonyl, $C_1$–$C_6$-alkoxycarbonyl, carbamoyl and $C_1$–$C_6$-alkylsulphonyl, by cyano, hydroxyl or mercapto, by $C_1$–$C_6$-alkylthio, $C_1$–$C_6$-alkylsulphinyl or $C_1$–$C_6$-alkylsulphonyl, each of which can be substituted in the alkyl part by hydroxyl, by methylthio, methylsulphinyl or methylsulphonyl, each of which is substituted in the methylthio by carboxyl or $C_1$–$C_6$-alkoxycarbonyl, by $C_2$–$C_6$-alkenylthio, $C_2$–$C_6$-alkenylsulphinyl or $C_2$–$C_6$-alkenylsulphonyl, by phenyl, benzyl or heteroaryl, each of which can also be substituted by halogen, by formyl or ketalized formyl, by $C_1$–$C_6$-alkylcarbonyl, which can also be substituted by hydroxy and can be in ketalized form, by arylcarbonyl or $C_1$–$C_6$-alkylcarbonylamino, by carboxyl or $C_1$–$C_6$-alkoxycarbonyl, and by sulphamyl, which can be monosubstituted on the nitrogen by $C_1$–$C_6$-alkylaminocarbonyl, and onto which an optionally substituted 3-membered to 7-membered, preferably 5-membered or 6-membered, ring can be fused, which can contain up to two hetero-atoms, preferably O, N or S, and up to two double bonds and can also be aromatic or heteroaromatic, and can be mono- or poly-substituted, but preferably monosubstituted, by the following substituents: $C_1$–$C_6$-alkyl, $C_3$–$C_7$-cycloalkyl, $C_1$–$C_4$-alkoxy, $C_1$–$C_4$-hydroxyalkyl, halogen, hydroxyl, oxo, hydroximino, exomethylene, carboxy, $C_1$–$C_6$-alkoxycarbonyl, cyano, carbamoyl, sulphamoyl, amino, $C_1$–$C_4$-alkylamino and $C_1$–$C_4$-dialkylamino.

Very particularly preferred compounds of the formula I are those in which $R_1$ represents $C_1$–$C_5$-alkyl, in particular methyl, and A is a pyridinium radical which is mono- or poly-substituted, preferably mono-, di- or tri-substituted and in particular mono- or di-substituted, for example by hydroxy-$C_1$–$C_4$-alkyl, such as, in particular, hydroxymethyl, hydroxyethyl, hydroxypropyl, hydroxyisopropyl, hydroxybutyl, hydroxy-sec.-butyl or hydroxy-tert.-butyl, it also being possible, for example, for the alkyl radical to contain two or three hydroxyl groups, carboxy-$C_1$–$C_4$-alkyl, such as, in particular, carboxymethyl and carboxyethyl, $C_1$–$C_4$-alkoxycarbonyl-$C_1$–$C_4$-alkyl, such as, in particular, methoxycarbonylmethyl, ethoxycarbonylmethyl and methoxycarbonylethyl, formyl-$C_1$–$C_4$-alkyl, such as, in particular, formylmethyl, $C_1$–$C_4$-alkylcarbonyl-$C_1$–$C_4$-alkyl, such as, in particular, methylcarbonylmethyl, ethylcarbonylmethyl, methylcarbonylethyl and ethylcarbonylethyl, the two alkyl groups of which can also additionally be substituted by hydroxyl and the carbonyl group of which can also be in ketalized form, carbamoyl-substituted $C_1$–$C_4$-alkyl, such as, in particular, carbamoylmethyl and carbamoylethyl, which can also be further substituted on the nitrogen by hydroxyl, such as, in particular, N-hydroxy-carbamoylmethyl, sulpho-$C_1$–$C_4$-alkyl, such as, in particular, sulphoethyl or 1-hydroxy-1-sulphomethyl, $C_1$–$C_4$-alkoxy-$C_1$–$C_4$-alkyl, such as, in particular, methoxymethyl, ethoxymethyl, propoxymethyl, isopropoxymethyl, methoxymethyl, ethoxyethyl, methoxypropyl and methoxyisopropyl, which can also be substituted by hydroxyl, such as, in particular, hydroxyethoxymethyl and hydroxyethoxyethyl, $C_1$–$C_4$-alkylthio-$C_1$–$C_4$-alkyl, such as, in particular, methylthiomethyl, ethylthiomethyl, methylthioethyl and ethylthioethyl, $C_1$–$C_4$-alkylsulphinyl-$C_1$–$C_4$-alkyl, such as, in particular, methylsulphinylmethyl, ethylsulphinylmethyl, methylsulphinylethyl and ethylsulphinylethyl, $C_1$–$C_4$-alkylsulphonyl-$C_1$–$C_4$-alkyl, such as, in particular, methylsulphonylmethyl, ethylsulphonylmethyl, methylsulphonylethyl and ethylsulphonylethyl, $C_3$-alkenyloxy-$C_1$–$C_4$-alkyl, such as, in particular, allyloxymethyl and allyloxyethyl, $C_3$-alkenylthio-$C_1$–$C_4$-alkyl, such as, in particular, allylthiomethyl, $C_3$-alkenylsulphinyl-$C_1$–$C_4$-alkyl, such as, in particular, allylsulphinylmethyl, $C_3$-alkenylsulphonyl-$C_1$–$C_4$-alkyl, such as, in particular, allylsulphonylmethyl, cyano-$C_1$–$C_3$-alkyl, such as, in particular, cyanomethyl and cyanoethyl, epoxy-$C_2$–$C_3$-alkyl, such as, in particular, epoxyethyl and epoxypropyl, trifluoromethyl, hydroximinomethyl and $C_1$–$C_3$-alkyloximinomethyl, such as, in particular, methoximinomethyl, $C_3$–$C_4$-alkenyl, such as, in particular, allyl, 2-methallyl and but-3-enyl, which can also be additionally substituted by hydroxyl, such as, in particular, hydroxyallyl and hydroxybutenyl, $C_3$-alkinyl, such as, in particular, propargyl, $C_3$–$C_6$-cycloalkyl and $C_3$–$C_6$-cycloalkyl-methyl, such as, in particular, cyclopropyl, cyclobutyl, cyclopentyl, cyclohexyl and cyclopentylmethyl, it being possible for the rings also to be substituted, for example by hydroxyl, such as, in particular, 1-hydroxy-1-cyclopentyl and 1hydroxy-1-cyclohexyl, or by halogen, preferably chlorine, or by carboxyl, $C_1$–$C_4$-alkoxycarbonyl or cyano, $C_5$–$C_6$-cycloalkenyl, such as, in particular, cyclopent-1-enyl and cyclohex-1-enyl, $C_1$–$C_4$-alkoxy, such as, in particular, methoxy, ethoxy, propoxy, isopropoxy, butoxy, isobutoxy and tert.-butoxy, preferably methoxy, it also being possible for these alkoxy groups to be additionally substituted, for example by hydroxyl, carboxyl or $C_1$–$C_4$-alkoxycarbonyl, in particular carboxymethoxy and methoxycarbonylmethoxy, epoxy-$C_2$–$C_3$-alkoxy, such as, in particular, epoxyethoxy or epoxypropoxy, $C_3$-alkenyloxy, such as, in particular, allyloxy, $C_3$-alkinyloxy, such as, in particular, propargyloxy, aryloxy, such as, in particular, phenoxy, amino, $C_1$–$C_5$-alkylamino, such as, in particular, ethylamino, $C_1$–$C_5$-dialkylamino, such as, in particular, dimethylamino and diethylamino, $C_1$–$C_4$-alkoxycarbonylamino, such as, in particular, methoxycarbonylamino and ethoxycarbonylamino, $C_1$–$C_4$-alkylcarbonylamino, such as, in particular, methylcarbonylamino, N-$C_1$–$C_4$-alkyl- and dialkylcarbamoylamino, such as, in-particular, N-methylcarbamoylamine and N,N-diethylcarbamoylamino, $C_1$–$C_4$-alkylsulphonylamino, such as, in particular, methyl- or ethyl-sulphonylamino, cyano, hydroxyl, in particular 3-hydroxy, $C_1$–$C_4$-alkylthio, such as, in particular, methylthio, ethylthio, propylthio and isopropylthio, which can also be substituted by hydroxyl, in particular hydroxyethylthio, $C_1$–$C_4$-alkylsulphinyl, such as, in particular methylsulphinyl, ethylsulphinyl, propylsulphinyl and isopropylsulphinyl, which can also be substituted by hydroxyl, in particular hydroxyethylsulphinyl, $C_1$–$C_4$-alkylsulphonyl, such as methyl-, ethyl-, propyl- or isopropyl-sulphonyl, which can also be substituted by hydroxyl, in particular hydroxyethylsulphonyl, carboxymethylthio and $C_1$–$C_4$-alkoxycarbonylmethylthio, in particular methoxycarbonylmethylthio, carboxymethyl-sulphinyl and -sulphonyl, and $C_1$–$C_4$-alkoxycarbonylmethyl-sulphinyl and -sulphonyl, in particular methoxycarbonylmethylsulphinyl and -sulphonyl, $C_3$-alkenylthio, such as allylthio and propr-1-enylthio, $C_3$-alkenylsulphinyl, such as allylsulphinyl and prop-1-enylsulphinyl, $C_3$-alkenylsulphonyl, such as allylsulphonyl and prop1-enylsulphonyl, phenyl and benzyl, which can also be substituted, for example by halogen, in particular chlorine, such as, for example, 4-chlorobenzyl, 2'-thienyl and 3'-thienyl, formyl and ketalized formyl, such as, for example, 1,3-dioxolan-2-yl, $C_1$–$C_4$-alkylcarbonyl, in particular acetyl and propionyl, preferably acetyl, which can also be substituted by hydroxyl and can be in ketalized form, such as, for example, 2-methyl1,3-dioxolan-2-yl, benzoyl, $C_1$–$C_4$-alkylcarbonylamino, in particular acetylamino and propionylamino, formylamino, carboxyl, for example also 2,3,4-carboxy, and $C_1$–$C_4$-alkoxycarbonyl, in particular methoxycarbonyl and ethoxycarbonyl, such as, for example, also 2,3,4-methoxy- or -ethoxy-carbonyl, and onto which an optionally substituted 5-membered or 6-membered ring can be fused, which can contain up to two heteroatoms, preferably from the group comprising O, N and S, and up to two double bonds and which can also be aromatic or heteroaromatic.

The following ring systems are particularly suitable fused-on rings: cyclopenteno, dihydrocyclopenteno, cyclohexeno, dehydrocyclohexeno, benzo, furo, dihydrofuro, pyrano, dihydropyrano, thieno, dihydrothieno, thiopyrano, dihydrothiopyrano, pyrido, dihydropyrido, tetrahydropyrido, pyrimido, dihydropyrimido, tetrahydropyrimido, pyrazino, dihydropyrazino, tetrahydropyrazino, pyridazino, dihydropyridazino and tetrahydropyridazino, each of which can be mono- or poly-substituted, but preferably monosubstituted, preferably by $C_1$–$C_4$-alkyl, such as, in particular, methyl, ethyl and isopropyl, $C_3$–$C_6$-cycloalkyl, such as, in particular, cyclopropyl, $C_1$–$C_4$-alkoxy, such as, in particular, methoxy and ethoxy, $C_1$–$C_3$-hydroxyalkyl, such as, in particular, hydroxymethyl and hydroxyethyl, halogen, such as, in particular, chlorine and fluorine, hydroxyl, carboxyl and cyano, $C_1$–$C_6$-alkoxycarbonyl, such as, in particular, methoxycarbonyl and ethoxycarbonyl, oxo and hydroximino, carbamoyl and sulphamoyl, amino, $C_1$–$C_4$-alkylamino, such as, in particular, methylamino and ethylamino, and $C_1$–$C_4$-dialkylamino, such as, in particular, diethylamino.

The compounds of the formula I are obtained by converting the acids of the formula II, wherein $R^2$ represents a customary protective group, into the mixed anhydrides of the formula III, reacting these with the compounds of the formula IV and subsequently splitting off the protective group $R^2$ from the resulting compounds of the formula V.

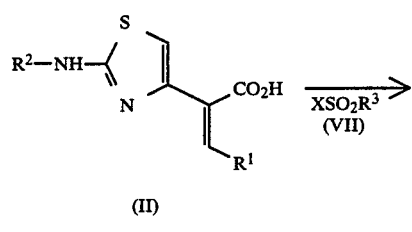

(II)

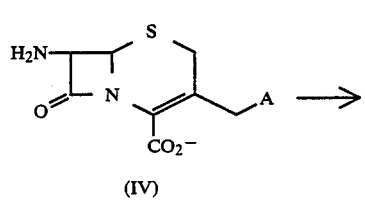

(III)

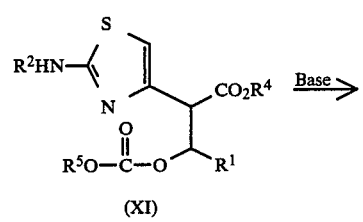

(IV)

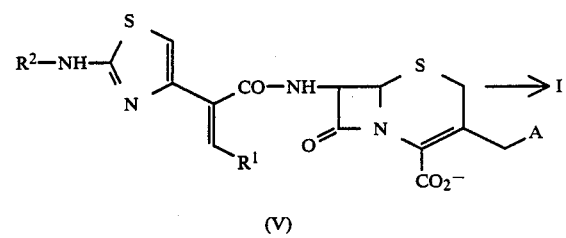

(V)

It is advantageous for the process to use a protective group which is unstable to acids, such as, for example tert.butoxycarbonyl, trityl or formyl, as the protective group $R^2$ and to carry out the splitting off of $R^2$ in V for the preparation of the compounds I according to the invention with an acid, for example trifluoroacetic acid or formic acid.

The compounds II and III can be prepared in accordance with the following equation:

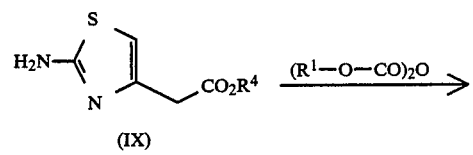

(IX)

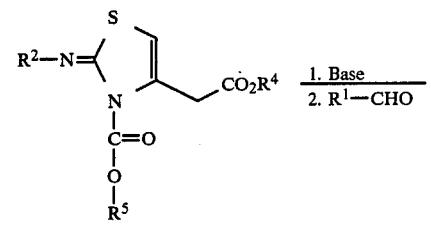

(X)

(In this process for the preparation of II, $R^2 \equiv R^5$—O—CO)

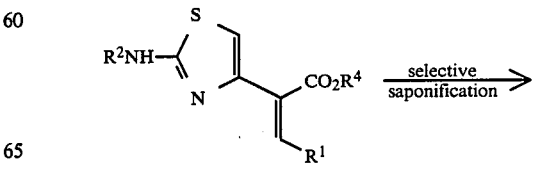

(XI)

(XII)

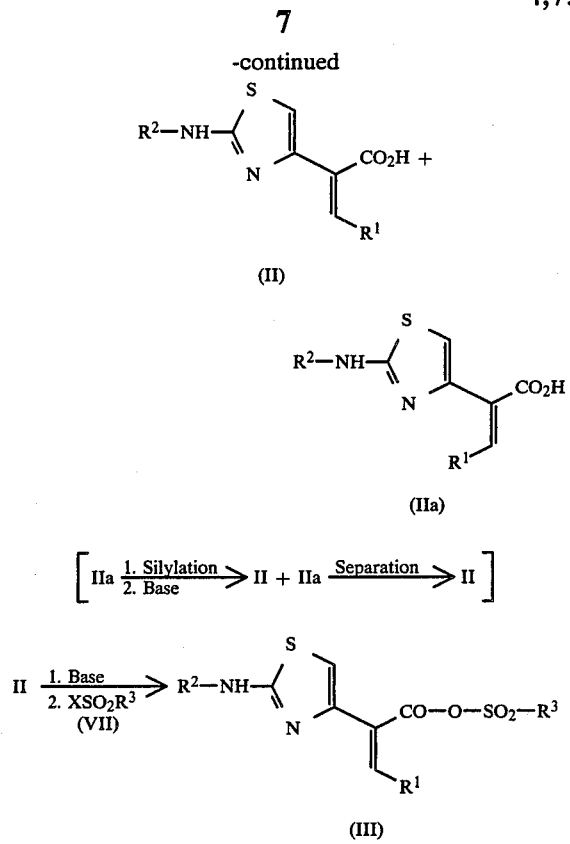

The compounds of the formula IX (see, for example, E. Campaigne and T. P. Selby, J. Heterocycl. Chem. 17 (1980), 1255) are first converted into the compounds of the formula X.

In formula X $R^2$ denotes an amine-protective group, such as, for example, acetyl, benzoyl, formyl, trichloroacetyl, benzyloxycarbonyl, methoxycarbonyl or tert.-butoxycarbonyl and $R^4$ and $R^5$, which can be identical or different, denote an optionally substituted alkyl, cycloalkyl, alkenyl, cycloalkenyl, aryl, or heterocyclyl radical, hertero-atoms in the heterocyclyl radicals and double bonds in the alkenyl and cycloalkenyl radicals being separated from the oxycarbonyl group by at least one C atom.

In particular, $R^4$ and $R^5$ are an optionally substituted alkyl radical with 1–15 C atoms, an optionally substituted alkenyl radical with 3–15 C atoms, an optionally substituted cycloalkyl radical with 3–10 C atoms, an optionally substituted cycloalkenyl radical with 5–10 C atoms, an optionally substituted aryl radical with 1 to 3 rings or an optionally substituted heterocyclyl radical with 1–3 rings which can contain up to 5 nitrogen, sulphur or oxygen atoms.

The alkyl, alkenyl, cycloalkyl and cycloalkenyl radicals $R^4$ and $R^5$ mentioned can be substituted by alkyl radicals with 1–4 C atoms, O-alkyl radicals with 1–4 C atoms, halogen, preferably chlorine, optionally substituted phenyl radicals, $C \equiv N$ and $C_1$–$C_5$-trialkylsilyl.

All the aryl and heterocyclyl radicals $R^4$ and $R^5$, including the phenyl radicals mentioned, can be substituted by alkyl, O-alkyl, S-alkyl, alkoxycarbonyl, halogen and phenyl radicals, it being possible for all the alkyl radicals to have 1 to 4 C atoms, and by nitro and $C \equiv N$.

If the radicals $R^4$ and/or $R^5$ are substituted, preferably by the abovementioned substituents, they can carry 1–5, preferably 1 or 2, substituents.

It is particularly advantageous for the process if $R^2$ is a protective group which is unstable to acids, such as, for example, tert.-butoxycarbonyl, and if $R^4$ is a radical which can be hydrolyzed under basic conditions, such as, for example, methyl or ethyl.

The compounds of the formula X are obtained by reacting the compounds of the formula IX, which are known per se, with a pyrocarbonic acid ester of the formula $R^5$—O-CO-O-CO-O-$R^5$ in a suitable solvent.

Particularly suitable solvents for this reaction are aprotic, polar solvents, such as, for example, acetonitrile, dimethylformamide, hexamethylphosphoric acid triamide or dimethylsulphoxide, especially the last two. The reaction proceeds particularly advantageously at room temperature or at lower temperatures, for example 0° to −50° C., the components being allowed to react with one another for 1–7 days. In general, 2–2.5 molar equivalents of the pyrocarbonic acid ester are used.

To prepare the compounds of the formula XI, 1 to 1.1 equivalents of a base are added to the compounds of the formula X in a suitable solvent at low temperatures, and 1 to 1.2 equivalents of an aldehyde of the formula $R^1$—CHO are then added.

Examples of solvents which can be used for the reaction are dimethylformamide, dimethylsulphoxide, diethyl ether, tetrahydrofuran and toluene—preferably tetrahydrofuran—and bases which can be used are alcoholates, hydrides, amides or metal-organyls—preferably potassium tert.-butylate, lithium diisopropylamide and butyl-lithium. For carrying out the reaction, the base is added to a solution of X at −50° to −80° C., the aldehyde is then added at −50° to −60° C. and the mixture is stirred at −50° to −60° C. for about 12 hours. For isolation of the products of the formula XI, the batch is neutralized and worked up.

In the compounds of the formula XI, $R^2$, $R^4$ and $R^5$ have the meanings listed in the case of the compounds of the formula X and $R^1$ has the abovementioned meaning.

For carrying out the process for the preparation of the compounds of the formula I, it is not necessary to isolate the compounds of the formula XI. Rather, it is advantageous to convert them in situ directly into the compounds of the formula XII. For this, it is in general sufficient to allow the batch to warm to room temperature, after addition of the aldehyde $R^1$—CHO, and to stir the batch at room temperature overnight. If the elimination from XI to give XII is then still not complete, 1 to 1.2 equivalents of a base—such as, for example, a hydride, an alcoholate or an amide—in particular potassium tert.-butylate, are added and the mixture is stirred at room temperature for about 10 hours.

In contrast, if the compound of the formula XI has first been isolated, the compounds of the formula XII are prepared by adding 1.1 to 2.2 equivalents of a base to a solution of the compounds of the formula XI in a suitable solvent. Solvents and bases which can be used are those mentioned for the conversion of X into XI, preferably tetrahydrofuran and potassium tert.-butylate.

The compounds of the formula XII are obtained as E/Z isomer mixtures which can be separated, for example, by recrystallization or by column chromatography on silica gel.

In the compounds of the formula XII, $R^1$, $R^2$ and $R^4$ have the same meaning as in the compounds of the formula XI.

To prepare the Z-carboxylic acids of the formula II, the Z-esters, which can be obtained by separation of the E/Z isomer mixtures of the esters of the formula XII, can be hydrolyzed. However, it is more advantageous for carrying out the process for the preparation of the compounds of the formula I to hydrolyze the E/Z isomer mixture of the esters of the formula XII selectively in a manner such that the E-esters are first converted into the E-carboxylic acids of the formula IIa under mild conditions and are separated off and the Z-esters which then remain, in which steric shielding of the ester group is greater, are then hydrolyzed to the Z-carboxylic acids of the formula II under drastic conditions.

The mild hydrolysis conditions which lead to the E-carboxylic acids IIa are, for example, ethanol/2 N sodium hydroxide solution/room temperature/24 hours. The hydrolysis is advantageously carried out in a manner such that, after the conversion of the compounds of the formula XI into the compounds of the formula XII, 2 N sodium hydroxide solution is added directly to the reaction batch and the batch is stirred at room temperature, or with slight warming, until the E-esters are hydrolyzed. The Z-esters are then separated off from the batch by extraction under alkaline conditions and are hydrolyzed under more drastic conditions.

More drastic hydrolysis conditions are, for example, ethanol/2 N sodium hydroxide solution/24 hours under reflux—if necessary also stronger sodium hydroxide solution or solvents with higher boiling points, such as, for example, dioxane.

The desired Z-carboxylic acids of the formula II and the E-carboxylic acids of the formula IIa are obtained in this manner. The latter can be converted back into a mixture of the E-carboxylic acids of the formula IIa and the Z-carboxylic acids of the formula II after conversion into the silyl ester—for example with bistrimethylsilylacetamide—in a suitable solvent—for example diethyl ether or tetrahydrofuran—with a base, such as potassium tert.-butylate, and by subsequent hydrolysis with dilute acid.

The Z-carboxylic acids of the formula II can be isolated in the pure form from this E/Z isomer mixture, for example, by crystallization or by separation on an ion exchanger.

Separation with the aid of ion exchangers is simple, since the Z-carboxylic acids of the formula II are very much more strongly acid than the E-carboxylic acids of the formula IIa. Thus, the E-carboxylic acids of the formula IIa are eluted from weakly basic ion exchangers with only methanol, whereas the Z-carboxylic acids of the formula II are eluted only after addition of electrolytes, for example 2 N sodium hydroxide solution. Weakly basic ion exchangers are to be understood as those ion exchangers, in solid or liquid form, which contain tertiary amino groups, such as, for example, Lewatit® MP 62.

In the compounds of the formula II and IIa, $R^1$ and $R^4$ have the same meaning as in the compounds of the formula XII. In addition, $R^4$ can be H, if $R^4$ in the compounds of the formula XII was a protective group which can be hydrolyzed under alkaline conditions, such as, for example, acetyl, before the hydrolysis. However, for carrying out the process for the preparation of the compounds of the formula I, it is more advantageous if $R^1$ is a protective group which is stable under the hydrolysis conditions—preferably tert.-butoxycarbonyl.

The compounds of the formula IV are obtained by reacting cephalosporins of the formula XIII, wherein $R^6$ represents a customary protective group, with noncharged nitrogen-containing heterocyclic compounds A', A' having the abovementioned meaning of A but not carrying the positive charge on the nitrogen, and then splitting off the protective group $R^6$ around the resulting compounds of the formula XIV.

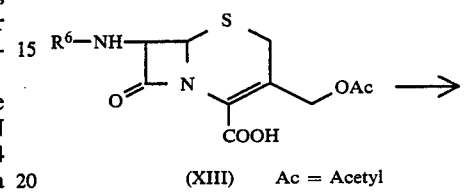

(XIII)   Ac = Acetyl

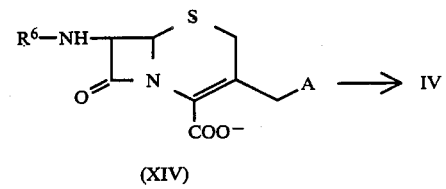

(XIV)

It is advantageous for the process if $R^6$ represents a protective group which can be split off either by the phosphoric acid chloride method customary in β-lactam chemistry or enzymatically.

The compounds of the formula XIII are converted into compounds of the formula XIV in organic or aqueous solvents, at temperatures between 20° C. and 100° C., preferably between 60° C. and 80° C., with addition of a suitable salt catalyst. An uncharged compound of the formula A', in which A' has the abovementioned meaning, is used here as the reagent.

Examples of suitable salt catalysts are NaBr, KI, KSCN, NaSCN and LiI.

A preferred organic solvent is dimethylformamide.

The reaction is particularly preferably carried out in aqueous solution, using a large excess of KSCN.

It is favorable to use the compound A' in a small excess, the addition of 1 equivalent of an inorganic base, preferably sodium bicarbonate, being advantageous.

The protective group $R^6$ in formula XIII is split off either with phosphorus pentachloride in a manner which is known from the literature or, preferably, enzymatically, with penicillin acylase. It is particularly advantageous for the enzymatic splitting off if $R^6$ is phenylacetyl or thienylacetyl. The splitting off is advantageously carried out in aqueous solution at pH 7–8.

A large number of methods, which are ultimately derived from peptide chemistry, are known in cephalosporin chemistry for coupling carboxylic acids to 7-aminocephalosporanic acids. However, in attempts to link the amide bond between the Z-carboxylic acids of the formula II and the cephalosporanic acids of the formula IV, these methods fail or lead only to very-poor yields, especially if $R^1$ is an alkyl radical. The reasons for this are the high steric hindrance of the carboxyl group in the carboxylic acids of the formula II by the radical $R^1$ and the marked tendency of the radical $R^1$, after activation of the carboxyl function—for example conversion into the acid chloride—to isomerize into the E-form.

However, the Z-carboxylic acids of the formula II can be activated in a simple, mild and inexpensive manner by converting them into the mixed anhydrides of the formula III at low temperatures.

Such mixed anhydrides of the formula III can be prepared by dissolving equimolar amounts of the carboxylic acid II and a suitable amine in a suitable solvent and allowing them to react with 1 to 1.05 equivalents of a sulphonic acid derivative of the formula VII.

Suitable solvents are all solvents which are stable under the reaction conditions, such as, for example, diethyl ether, tetrahydrofuran, acetonitrile, acetone, methylene chloride, chloroform or dimethylformamide.

Suitable amines are tertiary amines, such as, for example, triethylamine or tributylamine, and also sterically hindered secondary amines, such as, for example, diisopropylamine.

The reactions can be carried out at temperatures between $-80°$ C. and room temperature, low temperatures avoiding isomerization of the substituents on the double bond. The reactions are advantageously carried out at $-20°$ to $-50°$ C. in a reaction time of 10 minutes to 10 hours.

The compounds of the formula III can be isolated, for example, by using tetrahydrofuran as the solvent and triethylamine as the base, filtering off, with suction, the triethylamine hydrochloride formed and distilling off the solvent in vacuo. However, it is more advantageous to react the resulting solutions of the compounds of the formula III directly with the cephalosporinates of the formula IV. For this, the cephalosporinates of the formula IV, or salts thereof, are dissolved in a suitable solvent with 1-4 equivalents of an amine, the solution is precooled to the desired subsequent reaction temperature and this solution is added to the solution, described above, of the compound of the formula III at this temperature. To avoid isomerization of the radical $R^1$ in the reaction products of the formula V, the reaction is advantageously carried out at $-60°$ to $-30°$ C. and the batch is allowed to come to room temperature overnight.

To dissolve the compounds of the formula IV, the solvents mentioned for the preparation of the compounds of the formula III can be used, together with the amines mentioned in the same context, as the base.

In general, the solubility of the compounds of the formula IV in these solvents is very limited, so that silylation is advantageously carried out here in a manner which is known per se, or water is used as the solvent.

It is particularly advantageous to convert the carboxylic acids VI without a protective group into the mixed anhydrides of the formula VIII with the sulphonic acid derivatives VII and to react the anhydrides directly with IV to give the compounds of the formula I.

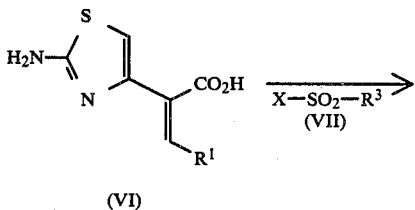

(VI)

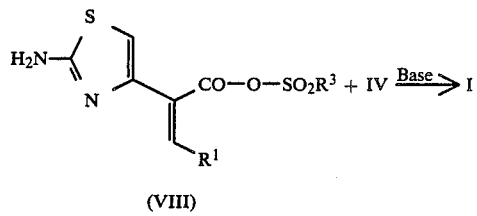

(VIII)

In these formulae,

X denotes Cl, Br or $OSO_2R^3$ and $R^3$ denotes an alkyl radical which has 1–10 C atoms and can optionally be substituted by fluorine, chlorine, CN, phenyl, alkoxycarbonyl, alkoxy or alkyl, it being possible for the latter alkyl radicals to carry 1–4 C atoms, or denotes a phenyl radical, which can optionally be substituted by fluorine, chlorine, bromine, CN, alkyl, alkoxy, alkylthio, alkoxycarbonyl—it being possible for the latter alkyl groups to carry 1–4 C atoms—nitro, trifluoromethyl and phenyl.

If $R^3$ is substituted, 1–3 substituents are preferably present, and preferably those mentioned.

$R^3$ very particularly preferably represents a methyl or p-tolyl radical.

The mixed anhydrides of the formula VIII are prepared analogously to the anhydrides of the formula III, by dissolving the carboxylic acids of the formula VI and 1–1.4 equivalents of an amine in a solvent and allowing the solution to react with 1 to 1.2 equivalents of a sulphonic acid derivative of the formula VII.

Suitable solvents are all the solvents which are stable under the reaction conditions, such as, for example, diethyl ester, tetrahydrofuran, acetonitrile, acetone, methylene chloride, chloroform or dimethylformamide.

Suitable amines are tertiary amines, such as, for example, triethylamine or tributylamine, or sterically hindered secondary amines, such as, for example, diisopropylamine.

The reactions can be carried out at temperatures between $-80°$ C. and room temperature, low temperatures avoiding isomerization of the substituents on the double bond. The reaction with $Cl-SO_2CH_3$ is advantageously carried out in dimethylformamide at $-40°$ to $-60°$ C.

To dissolve the compounds of the formula IV, the solvents mentioned for the preparation of the compounds of the formula VIII can be used, together with the amines mentioned in that context, as the base.

The solubility of the compounds of the formula IV in these solvents is in general very limited, so that silylation is advantageously carried out here in a manner which is known per se, or water is used as the solvent.

The compounds of the formula VI are obtained by splitting off the protective group $R^3$ from the compounds of the formula II—for example the Boc protective group with trifluoroacetic acid.

Another process for the preparation of the compounds of the formula I is the reaction of cephalosporins of the formula XV with uncharged nitrogen-containing heterocyclic compounds A', wherein A' and $R^1$ have the abovementioned meaning.

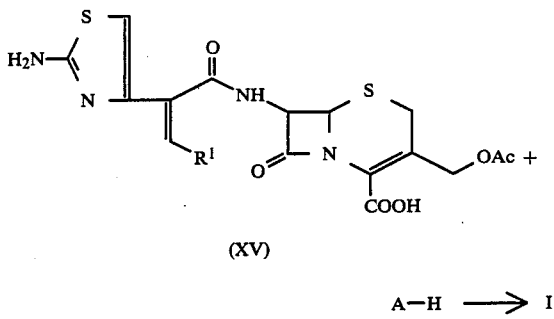

(XV)

A—H ⟶ I

The reaction is carried out in a polar organic solvent, such as dimethylformamide, or, preferably, in water or in a mixture of water and an organic solvent which is readily miscible with water, such as, for example, acetone, dioxane, acetonitrile, dimethylformamide, dimethylsulphoxide or ethanol. The reaction temperature is in general in the range from about 10 to about 100° C., preferably between 20° and 80° C. The pyridine component A' is added in amounts which are between approximately equimolar amounts and up to about a 5-fold excess. The exchange is facilitated by the presence of neutral salt ions, preferably iodide ions or thiocyanate ions, in the reaction medium. In particular, about 10 to about 30 equivalents of potassium iodide, sodium iodide, potassium thiocyanate or sodium thiocyanate are added. The reaction is advantageously carried out close to the neutral point, preferably at a pH value in the range from about 5 to about 8.

To isolate the products of the formula I, it is advantageous, after extraction of the pyridine A', to chromatograph the resulting crude product on a resin, such as, for example, Diaion HP 20 or XAD 7, or on cellulose.

The compounds of the formula I according to the invention can also be prepared from the compounds of the formula XV in a particularly preferred manner by intermediately producing a reactive iodide in a manner which is known from the literature (Tetrahedron Letters, 1981, 3915) in an organic solvent with trimethylsilyl iodide, and then reacting the iodide with uncharged heterocyclic bases A' to give compounds of the formula I.

The compounds of the formula XV can be obtained analogously to the compounds of the formula I according to the invention. For this, 7-aminocephalosporanic acid is merely used in the coupling of the compounds of the formula VIII, instead of the cephalosporinate of the formula IV.

The compounds according to the invention display a powerful and broad antimicrobial activity, especially against Gram-negative and Gram-positive bacteria. These properties enable them to be used as chemotherapeutic active compounds in medicine. With the aid of these compounds, it is possible to prevent, alleviate and/or cure the diseases caused by Gram-negative and Gram-positive bacteria and bacteria-like organisms.

The compounds according to the invention are particularly effective against bacteria and bacteria-like micro-organisms.

They are therefore particularly suitable, in human medicine and veterinary medicine, for the prophylaxis and chemotherapy of local and systemic infections caused by these pathogens.

For example, local and/or systemic diseases which are caused by the following pathogens or by mixtures of the following pathogens can be treated and/or prevented: Micrococcacae, such as Staphylococci, for example *Staphylo-coccus aureus, Staph. epidermidis, Staph. aerogenes* and *Gaffkya tetragena* (Staph. = Staphylococcus); Lactobacteriaceae, such as Streptococci, for example *Streptococcus pyogenes*, α and βhaemolysing Streptococci, noncoccus (γ-)-haemolysing Streptococci, *Str. viridans, Str. faecalis* (Enterococci) and *Dipolococcus pneumoniae* (Pneumococci) (Str. = Streptococcus); Enterobacteriaceae, such as Escherichiae bacteria of the coli group: Escherichia bacteria, for example *Escherichia coli*, Enterobacter bacteria, for example *E. aerogenes* and *E. Cloacae*, Klebsiella bacteria, for example *K. pneumoniae*, and Serratia, for example *Serratia marvescens* (E. = Enterobacter) (K. = Klebsiella), and Proteae bacteria of the Proteus group: Proteus, for example *Proteus vulgaris, Pr. morganii, P-r. rettgeri* and *Pr. mirabilis*, (Pr. = Proteus); Pseudomonadaceae, such as Pseudomonas bacteria, for example *Pseudomonas aeruginosa*, (Ps. = Pseudomonas); and Bacteroidaceae, such as Bacteroides bacteria, for example *Bacteroides fragilis*, (B. = Bacteroides).

The above list of pathogens is purely illustrative and is in no way to be interpreted as restrictive.

Examples which may be mentioned of diseases which can be prevented, alleviated and/or cured by the compounds according to the invention are: diseases of the respiratory passages and of the pharyngeal cavity; otitis; pharyngitis; pneumonia; peritonitis; pyelonephritis; cystitis; endocarditis; systemic infections; bronchitis; arthritis; and local infections.

The present invention includes pharmaceutical formulations which, in addition to non-toxic, inert pharmaceutically suitable excipients, contain one or more compounds according to the invention, or which consist of one or more active compounds according to the invention.

The present invention also includes pharmaceutical formulations in dosage units. This means that the formulation is in the form of individual parts, for example tablets, dragees, capsules, pills, suppositories and ampules of which the content of active compound corresponds to a fraction or a multiple of an individual dose. The dosage units can contain, for example, 1, 2, 3 or 4 individual doses or ½, ⅓ or ¼ of an individual dose. An individual dose preferably contains the amount of active compound which is given in one administration and which usually corresponds to a whole, a half, a third or a quarter of a daily dose.

By non-toxic, inter pharmaceutically suitable excipients there are to be understood solid, semi-solid or liquid diluents, fillers and formulation auxiliaries of every kind.

Tablets, dragees, capsules, pills, granules, suppositories and solutions, suspensions and emulsions, pastes, ointments, gels, creams, lotions, powders and sprays may be mentioned as preferred pharmaceutical formulations.

Tablets, dragees, capsules, pills and granules can contain the active compound or compounds alongside the customary excipients, such as (a) fillers and extenders, for example starches, lactose, sucrose, glucose, mannitol and silica, (b) binders, for example carboxymethylcellulose, alginates, gelatine and polyvinylpyrrolidone, (c) humectants, for example glycerol, (d) disintegrating agents, for example agar-agar, calcium carbonate and sodium carbonate, (e) solution retarders, for example paraffin, and (f) absorption accelerators, for example quaternary ammonium compounds, (g) wetting agents, for example cetyl alcohol and glycerol monostearate, (h) adsorbents, for example kaolin and bentonite, and (i) lubricants, for example talc, calcium magnesium stearate and solid polyethylene glycols, or mixtures of the substances listed under (a) to (i).

The tablets, dragees, capsules, pills and granules can be provided with the customary coatings and shells, optionally containing opacifying agents, and can also be of such composition that they release the active compound or compounds only, or preferentially, in a certain part of the intestinal tract, optionally in a delayed manner, examples of embedding compositions which can be used being polymeric substances and waxes.

The active compound or compounds, optionally together with one or more of the abovementioned excipients, can also be in a microencapsulated form.

Suppositories can contain, in addition to the active compound or compounds, the customary water-soluble or water-insoluble excipients, for example polyethylene glycols, fats, for example cacao fat, and higher esters (for example $C_{14}$-alcohol with $C_{16}$-fatty acid), or mixtures of these substances.

For parenteral administration, the solutions can also be in a sterile form which is isotonic with blood.

The therapeutically active compounds should preferably be present in the abovementioned pharmaceutical formulations in a concentration of about 0.1 to 99.5, preferably about 0.5 to 95, per cent by weight of the total mixture.

The abovementioned pharmaceutical formulations can also contain other pharmaceutical active compounds, in addition to the active compounds according to the invention.

The abovementioned pharmaceutical formulations are prepared in the customary manner according to known methods, for example by mixing the active compound or compounds with the excipient or excipients.

The active compounds or the pharmaceutical formulations can be administered locally, orally, parenterally, intraperitonally and/or rectally, preferably orally or parenterally, such as intravenously or intramuscularly.

In general, it has proved advantageous both in human medicine and in veterinary medicine to administer the active compound or compounds according to the invention in total amounts of about 1 to about 1,000, preferably 1 to 200, mg/kg of body weight every 24 hours, optionally in the form of several individual administrations, in order to achieve the desired results. An individual administration preferably contains the active compound or compounds according to the invention in amounts of about 1 to about 250, in particular 1 to 60, mg/kg of body weight. However, it may be necessary to deviate from the dosages mentioned, and in particular to do so as a function of the nature and body weight of the subject to be treated, the nature and severity of the disease, the nature of the formulation and of the administration of the medicament, and the time or interval over which the administration takes place. Thus, in some cases it can suffice to manage with less than the abovementioned amount of active compound, while in other cases the abovementioned amount of active compound must be exceeded. The particular optimum dosage required and the type of administration of the active compounds can easily be determined by anyone skilled in the art on the basis of his expert knowledge.

In order to broaden the spectrum of action, the active compounds according to the invention can be combined with another $\beta$-lactam antibiotic or with aminoglycoside antibiotics, such as, for example, gentamicin, sisomicin, kanamicin, amikacin or tobramicin.

The compounds according to the invention are particularly suitable for use in combating infectious diseases, in particular in combating bacterial infections.

EXAMPLE 1

7-Amino-3-(2-hydroxymethylpyridinium)methyl-3-cephem-4-carboxylate 16 g of 7-$\beta$-phenacetylamido-3-cephem-4-carboxylic acid were dissolved in 16 ml of water by adding 3.8 g of sodium bicarbonate. After addition of 72 g of potassium thiocyanate and 4.8 g of 2-hydroxymethylpyridine, the mixture was stirred at 60° C. for 5 hours. The reaction solution was diluted with 600 ml of water and then cooled in an ice-bath. The mixture was acidified to pH 2 by slow dropwise addition of 0.5 N hydrochloric acid. After 3 hours, the precipitate formed was filtered off with suction, washed with cold water, suspended in 100 ml of water and dissolved by neutralization to pH 7.8 with triethylamine. The phenacetyl protective group was then split off enzymatically at pH 7.8 by addition of 8 of penicillinacylase resin. When the splitting had ended, the enzyme resin was filtered off, the filtrate was acidified to pH 1 with concentrated hydrochloric acid and the hydrochloride of the title compound was then precipitated with acetone. Yield: 1.6 g.

$^1$H-NMR (D$_2$O) $\delta$- (ppm)=8.71 (1H, d, J=7, H-6-Py); 8.45 (1H, m, H-4-Py); 8.13 (1H, m, H-3-Py); 7.87 (1H, m, H-5-Py); 5.43 (2H, m, CH$_2$-Py); 5.25 (1H, d, J=6 Hz, H-7lactam); 5.13 (1H, d, J=6 Hz; Z-6-lactam); 4.94 (2H, bs, Py-CH$_2$—OH); 3.55 (1H, d, J=18 Hz, S—CH$_2$-); and 3.28 (1H, d, J=18 Hz, S—CH$_2$).

EXAMPLE 2

7-Amino-3-(3-hydroxymethylpyridinium)methyl-3-cephem-4- carboxylate

The preparation was carried out analogously to Example 1.

$^1$H-NMR (D$_2$O) $\delta$(ppm) =8.85 (1H, s, H-2-Py); 9.78 (1H, d, J=7 Hz, H-6-Py); 8.45 (1H, d, J=8 Hz, H-4-Py); 7.99 (1H, dd, J=7 Hz, J=8 Hz, H-5-Py); 5.54 (1H, d, J=15 Hz, CH$_2$-Py); 5.31 (1H, d, J=15 Hz, CH$_2$-Py); 5.26 (1H, d, J=5 Hz, H-7-lactam); 5.13 (1H, d, J=5 Hz, H-6-lactam); 4.80 (2H, s, Py-CH$_2$—OH); 3.63 (1H, d, J=18 Hz, S—CH$_2$); and 3.37 (1H, d, J=18 Hz, S—CH$_2$).

EXAMPLE 3

7-Amino-3-(4-hydroxymethylpyridinium)methyl-3-cephem-4-carboxylate

The preparation was carried out analogously to Example 1.

$^1$H-NMR (D$_2$O)$\delta$(ppm)=8.84 (2H, d, J=8 Hz, H-2, 6-Py); 8.02 (2H, d, J=8 Hz, H-3,5-Py); 5.62 (1H, d, J=15 Hz, CH$_2$-Py); 5.39 (1H, d, J=15 Hz, CH$_2$-Py); 5.37 (1H, d, J=5 Hz, H-7-lactam); 5.23 (1H, d, J=5 Hz, H-6-lactam); 4.98 (2H, s, Py-CH$_2$—OH); 3.74 (1H, d, H=18 Hz, S—CH$_2$); and 3.40 (1H, d, J=1Hz, S—CH$_2$).

EXAMPLE 4

7-Amino-3-(3-carboxymethylpyridinium)methyl-3-cephem-4-carboxylate

The preparation was carried out analogously to Example 1.

$^1$H-NMR (D$_2$O)δ(ppm)=8.85 (1H, s, H-2-Py); 8.80 (1H, d, J=7 Hz, H-6-Py); 8.43 (1H, d, J=8 Hz, H-4-Py); 7.99 (1H, m, H-5-Py); 5.54 (1H, d, J=14 Hz, CH$_2$-Py); 5.28 (1H, d, J=14 Hz, CH$_2$-Py); 5.23 (1H, d, J=5 Hz, H-7lactam); 5.11 (1H, d, J=5 Hz, H-6-lactam); 3.94 (2H, bs, Py-CH$_2$—); 3.60 (1H, d, J=18 Hz, S—CH$_2$); and 3.24 (1H, d, J=18 Hz, S—CH$_2$).

EXAMPLE 5

7-Amino-3-(4-carboxypyridinium)methyl-3-cephem-4-carboxylate

The preparation was carried out analogously to Example 1.

$^1$H-NMR (D$_2$O)δ(ppm)=9.03 (2H, d, J=7 Hz, H-2,6-Py); 8.38 (2H, d, J=7 Hz, H-3,5-Py); 5.74 (1H, d, J=15 Hz, CH$_2$-Py); 5.41 (1H, d, J=15 Hz, CH$_2$-Py); 5.31 (1H, d, J=5 Hz, H-7-lactam); 5.19 (1H, d, J=5 Hz, H-6-lactam); 3.72 (1H, d, J=18 Hz, S—CH$_2$); and 3.37 (1H, d, J=18 Hz, S—CH$_2$).

EXAMPLE 6

7-Amino-3-(4-cyclopropylpyridinium)methyl-3-cephem-4-carboxylate

The preparation was carried out analogously to Example 1.

$^1$H-NMR (D$_2$O)δ(ppm) =8.55 (2H, d, J=7 Hz, H-2,6-Py); 7.60 (2H, d, J=7 Hz, H-3,5-Py); 5.43 (1H, d, J=15 Hz, CH$_2$-Py); 5.27 (1H, d, J=5 Hz, H-7-lactam); 5.25 (1H, d, J=15 Hz, CH$_2$—Py); 3.60 (1H, d, J=18 Hz, S—CH$_2$); 3.28 (1H, d, J=18 Hz, S—CH$_2$); 2.18 (1H, m, cycloprop.); 1.40 (2H, m, cycloprop.); and 1.08 (2H, m, cycloprop.).

EXAMPLE 7

7-Amino-3-(4-benzylpyridinium)methyl-3-cephem-4-carboxylate

The preparation was carried out analouously to Example 1.

$^1$H-NMR (DMSO)δ(ppm) =9.06 (2H, d, J=7 Hz, H-2,6-Py); 8.11 (2H, d, J=7 Hz, H-3,5-Py); 7.20 - 7.30 (5H, m, arom.); 5.59 (1H, d, J=13 Hz, CH$_2$-Py); 5.50 (1H, d, J=13 Hz, CH$_2$-Py); 5.15 (1H, d, J=5 Hz, H-7-lactam), 5.03 (1H, d, J=5 Hz, H-6-lactam); 4.31 (2H, bs, CH$_2$φ; 3.60 (1H, d, J=18 Hz, S—CH$_2$); and 3.46 (1H, d, J=18 Hz, S—CH$_2$).

EXAMPLE 8

7-Amino-3-(4-phenylpyridinium)methyl-3-cephem-4-carboxylate

The preparation was carried out analogously to Example 1.

$^1$H-NMR (D$_2$O)δ(ppm) =8.78 (2H, d, J=7 Hz, H-2,6-Py); 8.18 (2H, d, J=7 Hz, H-3,5-Py); 7.81 (2H, m, arom.); 7.52 (3H, m, arom.); 5.42 (1H, d, J=15 Hz, CH$_2$-Py); 5.22 (1H, d, J=15 Hz, CH$_2$-Py); 5.20 (1H, d, J=5 Hz, H-7-lactam); 5.09 (1H, d, J=5 Hz, H-6-Py); 3.58 (1H, d, J=18 Hz, S—CH$_2$); and 3.23 (1H, d, J=18 Hz, S—CH$_2$).

EXAMPLE 9

7-Amino-3-(2,3-cyclopentenopyridinium)methyl-3-cephem-4-carboxylate

The preparation was carried out analogously to Example 1.

$^1$H-NMR (D$_2$O)δ(ppm) =8.56 (1H, d, J=7 Hz, H-6-Py); 8.35 (1H, d, J=8 Hz, H-4-Py); 7.82 (1H, m, H-5-Py); 5.61 (1H, d, J=15 Hz, CH$_2$-Py); 5.53 (1H, d, J=15 Hz, CH$_2$-Py); 5.39 (1H, d, J=5 Hz, H-7-lactam); 5.27 (1H, d, J=5 Hz, H6-lactam); 3.66 (1H, d, J=18 Hz, S—CH$_2$); 3.45 (1H, d, J=18 Hz, S—CH$_2$); 3.38 (2H, m, cyclopent.); 3.23 (2H, m, cyclopent.); and 2.35 (2H, m, cyclopent.).

EXAMPLE 10

7-Amino-3-(5,6,7,8-tetrahydroquinolinium)methyl-3-cephem4-carboxylate

The preparation was carried out analogously to Example 1.

$^1$H-NMR (D$_2$O)δ(ppm) =8.49 (1H, d, J=7 Hz, H-6-Py); 8.26 (1H, d, J=8 Hz, H-4-Py); 7.68 (1H, m, H-5-Py); 5.50 (1H, d, J=15 Hz, CH$_2$-Py); 5.41 (1H, d, J=15 Hz, CH$_2$-Py); 5.27 (1H, d, J=5 Hz, H-7-lactam); 5.14 (1H, d, J=5 Hz, H-6-lactam); 3.47 (1H, d, J=18 Hz, S—CH$_2$); 3.32 (1H, d, J=18 Hz, S—CH$_2$); 2.97 (2H, m, cyclohex.); 2.89 (2H, m, cyclohex.); 1.86 (2H, m, cyclohex.); and 1.73 (2H, m, cyclohex.).

EXAMPLE 11

7-Amino-3-isoquinoliniummethyl-3-cephem-4-carboxylate

The preparation was carried out analogously to Example 1.

$^1$H-NMR (D$_2$O)δ(ppm) =9.74 (1H, s, H-1-isoq.); 8.57 (1H, d, J=7 Hz, H-3-isoq.); 8.39 (2H, m, isoq.); 8.20 (2H, m, isoq.); 8.01 (1H, m, isoq.); 5.72 (1H, d, J=15 Hz, CH$_2$-isoq.); 5.49 (1H, d, J=15 Hz, CH$_2$-isoq.); 5.29 (1H, d, J=5 Hz, H-7-lactam); 5.16 (1H, d, J=5 Hz, H-6lactam); 3.68 (1H, d, J=18 Hz, S—CH$_2$); and 3.45 (1H, d, J=18 Hz, S—CH$_2$).

EXAMPLE 12

7-Amino-3-quinoliniummethyl-3-cephem-4-carboxylate

The preparation was carried out analogously to Example 1.

$^1$H-NMR (D$_2$O/DMSO-d$_6$)δ(ppm) =9.24 (1H, d, J=7 Hz, H-2-quin.); 9.16 (1H, d, J=8 Hz, H-4-quin.); 8.40 (2H, m, quin.); 8.22 (1H, m, quin.); 8.04 (2H, m, quin.); 6.00 (1H, d, J=15 Hz, CH$_2$-quin.); 5.85 (1H, d, J=15 Hz, CH$_2$-quin.); 5.21 (1H, d, J=5 Hz, H-7-lactam); 5.12 (1H, d, J=5 Hz, H-6-lactam); 3.44 (1H, d, J=18 Hz, SrCH$_2$); and 3.24 (1H, d, J=18 Hz, S—CH$_2$).

EXAMPLE 13

7-Amino-3-(4-methoxymethylpyridinium)methyl-3-cephem-4-carboxylate

The preparation was carried out analogously to Example 1.

$^1$H-NMR (D$_2$O)δ(ppm) =8.85 (2H, d, J=7 Hz, H-2,6-Py); 8.00 (2H, d, J=7 Hz, H-3,5-Py); 5.61 (1H, d, J=15 Hz, CH$_2$-Py); 5.33 (1H, d, J=15 Hz, CH$_2$-Py); 5.29 (1H, d, J=5 Hz, H-7-lactam); 5.19 (1H, d, J=5 Hz, H-6-lactam); 4.80 (2H, bs, Py—CH$_2$); 3.58 (1H, d, j=18 Hz, S—CH$_2$); and 3.47 (3H, s, OCH$_3$).

EXAMPLE 14

7-Amino-3-(4-methoxypyridinium)methyl-3-cephem-4-carboxylate

The preparation was carried out analogously to Example 1.

$^1$H-NMR (D$_2$O)δ(ppm) =8.65 (2H, d, J=7 Hz, H-2,6-Py); 7.45 (2H, d, J=7 Hz, H-3,5-Py); 5.40 (1H, d, J=15 Hz, CH$_2$-Py); 5.27 (1H, d, J=5 Hz, H-7-lactam); 5.18 (2H, m, CH$_2$-Py, H-6-lactam); 4.07 (3H, s, OCH$_3$); 3.63 (1H, d, J=18 Hz, S—CH$_2$); and 3.30 (1H, d, J=18 Hz, S—CH$_2$).

EXAMPLE 15

7-[1-(2-Aminothiazol-4-yl)-1(Z)-propenecarboxamido]-3-(4-hydroxymethylpyridinium)methyl-3-cephem-4-carboxylate Under nitrogen, 736 mg (4 mmol) of 1-(2-aminothiazol-4-yl)-1(Z)-propenecarboxylic acid were dissolved in 5 ml of absolute dimethylformamide, and 767 μl (4.4 mmol) of ethyl-diisopropylamine were added. After the mixture had been cooled to −55° C., 320 μl of methanesulphonyl chloride were added and the mixture was subsequently stirred for 40 minutes. Meanwhile, 1.50 g (4 mmol) of 7-amino-3-(4-hydroxymethylpyridinium)methyl-3-cephem-4-carboxylic acid chloride hydrate were dissolved in 2 ml of water, the pH was brought to 7 by addition of triethylamine and the solution was cooled to 10° C.. A further 2 ml of triethylamine were then added and the solution was then rapidly poured into the dimethylformamede solution, cooled to −55° C., with stirring. After 10 minutes, the reaction solution was poured onto 600 ml of acetone and the precipitate formed was filtered off with suction, dissolved in a little water and purified over adsorber resin HP 20 (elution with water and increasing amounts of acetonitrile). Finally, the product was lyophilized. Yield: 650 mg.

$^1$H-NMR (D$_6$-DMSO)δ(ppm)=9.35 (2H, d, J=7 Hz, H-2,6-Py); 9.18 (1H, d, J=9 Hz, NH); 8.03 (2H, d, J=7 Hz, H-3,5Py); 6.98 (2H, bs, NH$_2$); 6.38 (1H, q, J=8 Hz, C=CH); 6.17 (1H, s, thiazole); 5.67 (1H, dd, J=5 Hz, J=9 Hz, H-lactam); 5.62 (1H, d, J=14 Hz, CH$_2$-Py); 5.09 (1H, d, J=5 Hz, H-6-lactam); 5.08 (1H, d, J=14 Hz, CH$_2$-Py); 4.79 (2H, s, Py-CH$_2$); 3.54 (1H, d, J=18 Hz, S—CH$_2$); 3.06 (1H, d, J=18 Hz, S—CH$_2$); and 1.75 (3H, d, J=8 Hz, C=C—CH$_3$).

EXAMPLE 16

7-[1-(2-Aminothiazol-4-yl)-1(Z)-propenecarboxamido]-3-(3-hydroxymethylpyridinium) methyl-3-cephem-4-carboxylate The preparation was carried out analogously to Example 15.

$^1$H-NMR (D$_6$-DMSO)δ(ppm) =9.47 (1H, d, J=7 Hz, H-6Py); 9.35 (1H, s, H-2-Py); 9.23 (1H, d, J=9 Hz, NH); 8.53 (1H, d, J=8 Hz, H-4-Py); 8.18 (1H, m, H-5-Py); 7.01 (2H, bs, NH$_2$); 6.32 (1H, q, J=8 Hz, C=CH); 6.20 (1H, s, thiazole); 5.72 (2H, m, CH$_2$-Py, H-7-lactam); 5.18 (1H, d, J=18 Hz, CH$_2$-Py); 5.13 (1H, d, J=5 Hz, H-6-lactam); 4.74 (2H, s, Py—CH$_2$); 3.56 (1H, d, j=18 Hz, S—CH$_2$); 3.12 (1H, d, J=18 Hz, S—CH$_2$); and 1.77 (3H, d, J=8 Hz, C=C—CH$_3$).

EXAMPLE 17

7-[1-(2-Aminothiazol-4-yl)-1(Z)-propenecarboxamido]-3-(2-hydroxymethylpyridinium)methyl-3-cephem-4-carboxylate The preparation was carried out analogously to Example 15.

$^1$H-NMR (D$_6$-DMSO)δ (ppm) =9.37 (1H, d, J=7 Hz, H-6Py); 9.23 (1H, d, J=9 Hz, NH); 8.58 (1H, m, H-4-Py); 819 (1H, d, J=8 Hz, H-3-Py); 8.08 (1H, m, H-5-Py); 7.00 (2H, bs, NH$_2$); 6.32 (1H, q, J=8, Hz, C=CH); 6.20 (1H, s, thiazole); 5.71 (1H, dd, J=5 Hz, J=9 Hz, H-7-lactam); 5.46 (1H, d, J=14 Hz, CH$_2$-Py); 5.31 (1H, d, J=14 Hz, CH$_2$-Py); 5.11 (1H, d, J=5 Hz, H-6-lactam); 4.98 (2H, s, Py—CH$_2$); 3.46 (1H, d, J=18 Hz, S—CH$_2$); 3.08 (1H, d, J=18 Hz, S—CH); and 1.78 (3H, d, J=8 Hz, C=C—CH$_3$).

EXAMPLE 18

7-[1-(2-Aminothiazol-4-yl)-1(Z)-propenecarboxamido]-3-[4(2-sulphoethyl)pyridiniumlmethyl-3-cephem-4-carboxylate The preparation was carried out analogously to Example 15.

$^1$H-NMR (D$_6$-DMSO)δ(ppm) =9.32 (2H, d, J=7 Hz, H-2,6-Py); 9.20 (1H, d, J=9 Hz, NH); 8.06 (2H, d, J=7 Hz, H-3,5-Py); 6.97 (2H, bs, NH$_2$); 6.28 (1H, q, J=8 Hz, C=CH); 6.17 (1H, s, thiazole); 5.67 (1H, dd, J=5 Hz, J=9 Hz, H-7-lactam); 5.61 (1H, d, J=14 Hz, CH$_2$-Py); 5.10 (1H, d, J=5 Hz, H-6-lactam); 4.97 (1H, d, J=14 Hz, CH$_2$-Py); 3.53 (1H, d, J=18 Hz, S—CH$_2$); 3.17 (2H, t, J=8, Py-CH$_2$—CH$_2$); 3.02 (1H, d, J=18 Hz, S—CH2); 2.84 (2H, t, J=8 Hz, Py CH$_2$—CH$_2$); and 1.75 (3H, d, J=8 Hz, C=C—CH$_3$).

EXAMPLE 19

7-[1-(2-Aminothiazol-4-yl)-1(Z)-propenecarboxamid-3-(4-carboxypyridinium)methyl-3-cephem-4-carboxylate The preparation was carried out analogously to Example 15.

$^1$H-NMR (D$_6$-DMSO)δ(ppm) =9.19 (2H, d, J=7 Hz, H-2,6Py); 9.12 (1H, d, J=9 Hz, NH); 8.15 (2H, d, J=7 Hz, H-3,5Py); 6.91 (2H, bs, NH$_2$); 6.23 (1H, q, J=8 Hz, C=CH); 6.12 (1H, s, thiazole); 5.65 (1H, dd, J=5 Hz, J=9 Hz, H-7-lactam); 5.57 (1H, d, J=13 Hz, CH$_2$-Py); 5.10 (1H, d, J=13 Hz, CH$_2$-Py); 5.06 (1H, d, J=5 Hz, H-6-lactam); 3.48 (1H, d, J=18 Hz, S—CH$_2$); 3.10 (1H, d, J=18 Hz, S—CH$_2$); and 1.73 (3H, d, J=8 Hz, C=C—CH$_3$).

EXAMPLE 20

7-[1-(2-Aminothiazol-4-yl)-1(Z)-propenecarboxamido]-3-(3-carboxypyridinium)methyl-3-cephem-4-carboxylate The preparation was carried out analogously to Example 15.

$^1$H-NMR (D$_6$-DMSO)δ(ppm) =9.48 (1H, s, H-2-Py); 9.42 (1H, d, J=7 Hz, H-6-Py); 9.21 (1H, d, J=9 Hz, NH); 8.75 (1H, d, J=8 Hz, H-4-Py); 8.05 (1H, m, H-5-Py); 6.95 (2H, bs, NH$_2$); 6.29 (1H, q, J=8 Hz, C=CH); 6.17 (1H, s, thiazole); 5.70 (2H, m, CH$_2$-Py, H-7-lactam); 5.18 (1H, d, J=14 Hz, CH$_2$-Py); 5.09 (1H, d, J=5 Hz, H-6-lactam); 3.51 (1H, d, J=18 Hz, S—CH$_2$); 3.03 (1H, d, J=18 Hz, S—CH$_2$); and 1.76 (3H, d, J=8 Hz, C=C—CH$_3$).

EXAMPLE 21

7-[1-(2-Aminothiazol-4-yl)-1(Z)-propenecarboxamido]-3-(3-carboxymethylpyridinium)methyl-3-cephem-4-carboxylate The preparation was carried out analogously to Example 15.

$^1$H-NMR (D$_6$-DMSO)δ(ppm) =9.43 (1H, d, J=7 Hz, H-6-Py); 9.27 (1H, s, H-2-Py); 9.21 (1H, d, J=9 Hz, NH); 8.46 (1H, d, J=8 Hz, H-4-Py); 8.09 (1H, m, H-5-Py); 6.99 (2H, bs, NH$_2$); 6.30 (1H, q, J=8 Hz, C=CH); 6.18 (1H, s, thiazole); 5.70 (2H, m, CH$_2$-Py, H-7-lactam); 5.12 (2H, m, CH$_2$-Py, H-6-lactam); 3.69 (2H, bs, Py-CH$_2$); 3.56 (1H, d, J=18 Hz, S—CH$_2$); 3.09 (1H, d, J=18 Hz, S—CH$_2$); and 1.76 (3H, d, J=8 Hz, C=C—CH$_3$).

EXAMPLE 22

7-[1-(2-Aminothiazol-4-yl)-1(Z)-propenecarboxamido]-3-(4-cyclopropylpyridinium)methyl-3-cephem-4-carboxylate The preparation was carried out analogously to Example 15.

$^1$H-NMR (D$_6$-DMSO)δ(ppm) =9.21 (2H, d, J=7 Hz, H-2,6-Py); 9.17 (1H, d, J=9 Hz, NH); 7.82 (2H, d, J=7 Hz, H-3,5-Py); 6.98 (2H, bs, NH$_2$); 6.20 (1H, q, J=8 Hz, C=CH); 6.18 (1H, s, thiazole); 5.67 (1H, dd, J=5 Hz, J=9 Hz, H-7-lactam); 5.55 (1H, d, J=15 Hz, CH$_2$-Py); 5.09 (1H, d, J=5 Hz, H-6lactam); 4.98 (1H, d, J=15 Hz, CH$_2$-Py); 3.53 (1H, d, J=18 Hz, S—CH$_2$); 3.04 (1H, d, J=18 Hz, S—CH$_2$); 2.28 (1H, m, cycloprop.); 1.77 (3H, d, J=8 Hz, C=C—CH$_3$); 1.39 (2H, m, cycloprop.) and 1.14 (2H, m, cycloprop.).

EXAMPLE 23

7-[1-(2-Aminothiazol-4-yl)-1(Z)-propenecarboxamido]-3-(4-phenylpyridinium)methyl-3-cephem-4-carboxylate The preparation was carried out analogously to Example 15.

$^1$H-NMR (D$_6$-DMSO) (ppm) =9.51 (2H, d, J=7 Hz, H-2,6-Py); 9.18 (1H, d, J=9 Hz, NH); 8.52 (2H, d, J=7 Hz, H-3,5-Py); 8.06 (2H, m, arom.); 7.65 (3H, m, arom.); 6.96 (2H, bs, NH$_2$); 6.28 (1H, q, J=8 Hz, C=CH); 6.17 (1H, s, thiazole); 5.65 (2H, m, CH$_2$-Py, H-7-lactam); 5.11 (1H, d, J=5 Hz, H-6-lactam); 5.06 (1H, d, J=14 Hz, CH$_2$-Py); 3.56 (1H, d, - J=18 Hz, S—CH$_2$); 3.11 (1H, d, J=18 Hz, S—CH$_2$); and 1.75 (3H, d, J=8 Hz, C=C—CH$_3$).

EXAMPLE 24

7-[1-(2-Aminothiazol-4-yl)-1(Z)-propenecarboxamido]-3-(4-benzylpyridinium)methyl-3-cephem-4-carboxylate The preparation was carried out analogously to Example 15.

$^1$H-NMR (D$_6$-DMSO)δ(ppm) =9.33 (2H, d, J=7 Hz, H-2,6-Py); 9.14 (1H, d, J=9 Hz, NH); 8.00 (2H, d, J=7 Hz, H-3,5-Py); 7.20–7.40 (5H, m, arom.); 6.97 (1H, s, thiazole); 6.27 (1H, q, J=8 Hz, C=CH); 6.15 (1H, s, thiazole); 5.65 (1H, dd, J=5 Hz, J=9 Hz, H-7-lactam); 5.56 (1H, d, J=13 Hz, CH$_2$-Py); 5.07 (1H, d, J=5 Hz, H-6-lactam); 4.99 (1H, d, J=13 Hz, CH$_2$-Py); 4.22 (2H, bs, Py-CH$_2$-φ); 3.50 (1H, d, j=18 Hz, S—CH$_2$); 3.03 (1H, d, J=18 Hz, S—CH$_2$); and 1.73 (3 H, d, J=8 Hz, C=C—CH$_3$).

EXAMPLE 25

7-[1-(2-Aminothiazol-4-yl)-1(Z)-propenecarboxamido]-3(2,3-cyclopentenopyridinium)methyl-3-cephem-4-carboxylate The preparation was carried out analogously to Example 15.

$^1$H-NMR (D$_6$-DMSO) δ (ppm) =9.31 (1H, d, J=7 Hz, H-6-Py); 9.22 (1H, d, J=9 Hz, NH); 8.37 (1H, d, J=8 Hz, H-4-Py); 7.91 (1H, dd, J=7 Hz, J=8 Hz, H-5-Py); 7.01 (2H, bs, NH$_2$); 6.32 (1H, q, J=8 Hz, C=CH); 6.20 (1H, s, thiazole); 5.69 (1H, dd, J=5 Hz, J=9 Hz, H-7-lactam); 5.49 (1H, d, J=13 Hz, CH$_2$-Py); 5.22 (1H, d, J=13 H, CH$_2$-Py); 5.09 (1H, d, J=5 Hz, H-6-lactam); 3.42 (3H, m, S—CH$_2$, cyclopent.); 3.13 (3H, m, S—CH$_2$, cyclopent.); 2.23 (2H, m, cyclopent.); and 1.7 (3H, d, J=8 Hz, C=C—CH$_3$).

EXAMPLE 26

7-[1-(2-Aminothiazol-4-yl)-1(Z)-propenecarboxamido]-3(5,6,7,8-tetrahydroquinolinium)methyl-3-cephem-4-carboxylate The preparation was carried out analogously to Example 15.

$^1$H-NMR (D$_6$-DMSO) δ (ppm) =9.22 (2H, m, NH, H-6-Py); 8.29 (1H, d, J=8 Hz, H-4-Py); 7.91 (1H, m, H-5-Py); 7.00 (2H, bs NH$_2$); 6.32 (1H, q, J=8 Hz, C=CH); 6.20 (1H, s, thiazole); 5.70 (1H, dd, J=5 Hz, J=9 Hz, H-7-lactam); 5.40 (2H, m, CH$_2$-Py); 5.11 (1H, d, J=5 Hz, H-6-lactam; 3.45 (1H, d, J=18 Hz, S-CH$_2$); 3.15 (3H, m, S-CH$_2$-cyclohex.); 2.95 (2H, m, cyclohex.); 1.89 (2H, m, cyclohex.); and 1.78 (5H, m, cyclohex., C=C-CH$_3$).

EXAMPLE 27

7-[1-(2-Aminothiazol-4-yl)-1(Z)-propenecarboxamido]-3-quinoliniummethyl-3-cephem-4-carb The preparation was carried out analogously to Example 15.

$^1$H-NMR (D$_6$-DMSO) δ (ppm)=9.73 (1H, d, J=7, H-2-quin.); 9.29 (1H, d, J=Hz, quin.); 9.18 (1H, d, J=8 Hz, NH); 9.11 (1H, d, J=8 Hz, quin.); 8.48 (1H, d, J=8 Hz, quin.); 8.23 (2H, m, quin.); 04 (1H, m, quin.); 6.97 (2H, bs, NH$_2$); 6.29 (1H, q, J=8 Hz, C=CH); 6.18 (1H, s, thiazole); 6.05 (1H, d, J=13 Hz, CH$_2$-quin.); 5.91 (1H, d, J=13 Hz, CH$_2$-quin.); 5.66 (1H, dd, J=8 Hz, J=5 Hz, H-7-lactam); 5.07 (1H, d, J=5 Hz, H-6-lactam); 3.40 (1H, d, J=18 Hz, S—CH$_2$); 3.00 (1H, d, J=18 Hz, S—CH$_2$); and 1.76 (3H, d, J=8 Hz, C=C—CH$_3$).

EXAMPLE 28

7-[1-(2-Aminothiazol-4-yl)-1(Z)-propenecarboxamido]-3-iso- quinoliniummethyl-3-cephem -4-carbonoxylate The preparation was carried out analogously to Example 15.

$^1$H-NMR (D$_6$-DMSO) δ (ppm)=10.26 (1H, s, H-1-isoquin.); 9.42 (1H, d, J=Hz, H-3-isoquin.); 9.19 (1H, d, J=9 Hz, NH); 8.59 (1H, d, J=7 Hz, isoquin.); 48 (1H, d, J=8 Hz, isoquin.); 8.29 (2H, m, isoquin.); 8.05 (1H, m, isoq.); 6.96 (2H, bs, NH$_2$); 6.28 (1H, q, J=8 Hz, C=CH); 6.16 (1H, s, thiazole); 5.83 (1H, d, J=14 Hz, CH$_2$-isoquin.); 5.67 (1H, dd, J=5 Hz, J=9 Hz, H-7-lactam); 5.24 (1H, d, J=14 Hz, isoq.); 5.11 (1H, d, J=5 Hz, H-6-lactam); 3.56 (1H, d, J=18 Hz, S—CH$_2$); 3.19 (1H, d, J=18 Hz, S—CH$_2$); and 1.73 (3H, d, J=8 Hz, C=C—CH$_3$).

EXAMPLE 29

7-[1-(2-Aminothiazol-4-yl)-1(Z)-propenecarboxamido]-3-(4-methoxymethylpyridinium)methyl-3-cephem-4-carboxylate The preparation was carried out analogously to Example 15.

$^1$H-NMR (D$_6$-DMSO) δ (ppm)=9.42 (2H, d, J=7 Hz, H-2,6-Py); 9.16 (1H, d, J=9 Hz; NH); 8.03 (2H, d, J=7 Hz, H-3,5-Py); 6.97 (2H, bs, NH$_2$); 6.29 (1H, q, J=8 Hz, C=CH); 6.18 (1H, s, thiazole); 5.65 (2H, m, CH$_2$-Py, H-7-lactam); 5.09 (1H, d, J=5 Hz, H-6-lactam); 5.06 (1H, d, J=14 Hz, CH$_2$-Py); 4.75 (2H, s, Py—CH$_2$); 3.54 (1H, d, J=18 Hz, S—CH$_2$); 3.43 (3H, s, OCH$_3$); 3.04 (1H, d, J=18 Hz, S—CH$_2$); and 1.76 (3H, d, J=8 Hz, C=C—CH$_3$).

EXAMPLE 30

7-[1-(2-Aminothiazol-4-yl)-1(Z)-propenecarboxamido]-3-(4-methoxypyridinium)methyl-3-cephem-4-carboxylate The preparation was carried out analogously to Example 15.

$^1$H-NMR (D$_6$-DMSO) δ (ppm)=9.30 (2H, d, J=7 Hz, H-2,6 -Py); 9.17 (1H, d, J=9 Hz, NH); 7.65 (2H, d, J=7 Hz, H-3,5-Py); 6.97 (2H, bs, NH$_2$); 6.29 (1H, q, J=8 Hz, C=CH); 6.18 (1H, s, thiazole); 5.65 (1H, dd, J=9 Hz, J=5 Hz, H-7-lactam); 5.49 (1H, d, J=14 Hz, CH$_2$-Py); 5.09 (1H, d, J=5 Hz, H-6-lactam); 4.87 (1H, d, J=14 Hz, CH$_2$-Py); 4.08 (3H, s, OCH3); 3.53 (1H, d, J=18 Hz, S—CH$_2$); 2.98 (1H, d, J=18 Hz, S—CH$_2$); and 1.75 (3H, d, J=8 Hz, C=C—CH$_3$).

The following compounds were prepared analogously to Example 15:

EXAMPLE 31

7-[1-(2-Aminothiazol-4-yl)-1(Z)-propenecarboxamido]-3-(2,3-dihydroxymethylpyridinium)methyl-3-cephem-4-carboxylate

EXAMPLE 32

7-[1-(2-Aminothiazol-4-yl)-1(Z)-propenecarboxamido]-3-(2-methyl-3-hydroxymethylpyridinium)methy-3-cephem-4-carboxylate

EXAMPLE 33

7-[1-(2-Aminothiazol-4-yl)-1(Z)-propenecarboxamido]-3-[4dimethylaminopyridinium]methyl-3-cephem-4-carboxylate

EXAMPLE 34

7-[1-(2-Aminothiazol-4-yl)-1(Z)-propenecarboxamido]-3-[3-methylisoquinolinium]methyl-3-cephem-4-carboxylate

EXAMPLE 35

7-[1-(2-Aminothiazol-4-yl)-1(Z)-propenecarboxamido]-3-(5-hydroxymethylquinolinium)methyl-3-cephem-4-carboxylate

EXAMPLE 36

7-[1-(2-Aminothiazol-4-yl)-1(Z)-propenearboxamido]-3-pyridazinium-3-cephem-4-carboxylate $^1$H-NMR (D$_6$-DMSO) δ (ppm)=10.41 (1H, d, J=7 Hz, pyrid.); 9.67 (1H, d, J=4 Hz, pyrid.); 9.18 (1H, d, J=9 Hz, NH); 8.74 (1H, m, pyrid.); 8.59 (1H, m, pyrid.); 6.98 (2H, bs, HN$_2$); 6.3 (1H, q. J=8 Hz, C=CH); 6.17 (1H, s, thiazole); 5.89 (1H, d, J=14 Hz, CH$_2$-pyrid.); 5.68 (1H, d, J=9 Hz, J=5 Hz, H-7-lactam); 5.37 (1H, d, J=14 Hz, CH$_2$-pyrid.); 5.06 (1H, d, J=5 Hz, H-6-lactam); 3.60 (1H, d, J=18 Hz, S—CH$_2$); 3.34 (1H, d, J=1Hz, S—CH$_2$); 3.34 (1H, d, J=18 Hz, S—CH$_2$); and 1.73 (3H, d, J=8 Hz, C=C—CH$_3$).

EXAMPLE 37

7-[1-(2-Aminothiazol-4-yl)-1(Z)-propenecarboxamido]-3-pyrazinium-3-cephem-4-carboxylate

EXAMPLE 38

7-[Z-2-(2-Aminothiazol-4-yl)-2-(2,3,6-trichlorobenzylidene)acetamido]-3-(3-carboxypyridinium)methyl-3-cephem-4-carboxylate 0.4 g of 1-hydroxybenzotriazole and 0.6 g of dicyclohexylcarbodiimide are added to a solution of 1 g of Z-2-(2-aminothiazol-4-yl)-2-(2,3,6-trichlorobenzylidene)acetic acid in 10 ml of absolute dimethylformamide and the mixture is stirred at room temperature for four hours. The mixture is filtered with suction and a solution of 1.3 g of 7-amino-3-(3-carboxypyridinium)-methyl-3-cephem-4carboxylic acid hydrochloride hydrate in 5 ml of water, which has been brought to pH 7.0 by addition of triethylamine, is added to the filtrate. After the mixture has been stirred at room temperature for two hours, 900 ml of acetone are stirred in and the product which has precipitated is filtered off with suction. Yield: 1.2 g.

$^1$H-NMR (DMSO) δ (ppm)=9.62 (1) bs, 9.40 (1) d, J=6 Hz, 9.10 (1) d, J=7 Hz, 8.80 (1) d, J=7 Hz, 8.11 (1) dd, J=7 Hz, J=6 Hz, 7.55 (1) d, J=9 Hz, 7.45 (1) d, J=9 Hz, 7.28 (2) bs, 7.17 (1) s, 6.62 (1) s, 5.71 (d) d, J=13 Hz, 5.60 (1) dd, J=7 Hz, J=5 Hz, 5.31 (1) d, J=13 Hz, 5.00 (1) d, J=5 Hz, 3.23 (1) d, J=17 Hz, 3.03 (1) d, J=17 Hz.

EXAMPLE 39

7-[Z-2-(2-Aminothiazol-4-yl)-(2,3,6-trichlorobenzylidene)acetamido]-3-(4-carboxypyridinium)methyl-3-cephem-4-carboxylate The preparation was carried out analogously to EXAMPLE 38.

EXAMPLE 40

7-[Z-2-(2-Aminothiazol-4-yl)-2-(2,3,6-trichlorobenzylidene)acetamido]-3-(3-carboxymethylpyridinium)-methyl-3-cephem-4-carboxylate The preparation was carried out analogously to Example 38.

EXAMPLE 41

7-Z-2-(2-Aminothiazol-4-yl)-2-benzylideneacetamido-3-(3-carboxypyridinium)methyl-3-cephem-4-carboxylate The preparation was carried out analogously to EXAMPLE 38, using Z-2-(2-aminothiazol-4-yl)-2-benzylideneacetic acid and 7-amino-3-(3-carboxypyridinium)methyl-3-cephem-4-carboxylic acid hydrochloride hydrate.

$^1$H-NMR (D$_2$O) δ (ppm)=9.18 (1) s, 8.90 (1) d, J=7 Hz, 77 (1) d, J=7 Hz, 7.99 (1) t, J=7 Hz, 7.31 (5) bs, 7.20 (1) s, 6.54 (1) s, 5.73 (1) d, J=5 Hz, 5.49 (1) d, J=14 Hz, 5.24 (1) d, J=14 Hz, 5.12 (1) d, J=5 Hz, 3.47 (1) d, J=17 Hz, 3.00 (1) d, J=17 Hz.

EXAMPLE 42

7-[Z-2-(2-Aminothiazol-4-yl)-2-benzylideneacetamido]-3-(4-hydroxymethylpyridinium)methyl-3-cephem-4-carboxylate The preparation was carried out analogously to Example 38, using Z-2-(2-aminothiazol-4-yl)-2-benzylideneacetic acid and 7-amino-3-(4-hydroxyethylpyridinium)-3-cephem-4-carboxylic acid hydrochloride hydrate.

$^1$H-NMR (DMSO/CD$_3$OD) δ (ppm)=9.23 (2) d, J=7 Hz, 8.00 (2) d, J=7 Hz, 7.1–7.5 (6) m, 6.38 (1) s, 5.70 (1) d, J=5 Hz, 5.63 (1) d, J=13 Hz, 5.12 (1) d, J=5 Hz, 5.10 (1) d, J=13 Hz, 4.77 (2) bs, 3.50 (1) d, J=18 Hz, 3.04 (1) d, J=18 Hz.

EXAMPLE 43

7-Amino-3-[4-(3-hydroxypropyl)pyridinium]methyl-3-cephem-4-carboxylate

The preparation was carried out analogously to Example 1.

$^1$H-NMR (D$_2$O) δ (ppm)=8.82 (2H, d, J=8 Hz, H-2,6-Py); 8.00 (2H, d, J=8 Hz, H-3,5-Py); 5.54 (1H, d, J=14 Hz, CH$_2$-Py); 5.37 (1H, d, J=14 Hz, CH$_2$-Py); 5.35 (1H, d, J=5 Hz, H-7-lactam); 5.23 (1H, d, J=5 Hz, H-6-lactam); 3.72 (1H, d, J=18Hz, S—CH$_2$); 3.6(2H, t, J=7 Hz, Py—CH$_2$); 3.35 (1H, d, J=18 Hz, S—CH$_2$); 3.05 (2H, t, J=7 Hz, —CH$_2$—OH); and 2.01 (2H, m, —CH$_2$—).

EXAMPLE 44

7-[1-(2-Aminothiazol-4-yl)-1(Z)-propenecarboxamido]-3-[4-(3-hydroxypropyl)pyridinium]methyl-3-cephem-4-carboxylate The preparation was carried out analogously to Example 15.

$^1$H-NMR (D$_6$-DMSO) δ (ppm)=9.35 (2H, d, J=8 Hz, H-2,6-Py); 9.18 (1H, d, J=9 Hz, NH); 8.03 (2H, d, J=8 Hz, H-3,5-Py), 6.97 (2H, bs, NH$_2$); 6.30 (1H, q, J=8 Hz, C=C—H); 6.18 (1H, s. thiazole); 5.69 (1H, dd, J=9 Hz, J=5 Hz, H-7-lactam); 5.62 (1H, d, J=14 Hz, CH$_2$-Py); 5.10 (1H, d, J=5 Hz, H-6-lactam); 5.01 (1H, d, J=14 Hz, CH$_2$-Py); 3.52 (1H, d, J=18 Hz, S—CH$_2$); 3.44 (2H, m, Py-CH$_2$—); 3.03 (1H, d, J=18 Hz, S—CH$_2$); 2.90 (2H, m, —CH$_2$—OH); 1.80 (2H, m, —CH$_2$—); and 1.75 (3H, d, J=8 Hz, C=C—CH$_3$).

EXAMPLE 45

7-Amino-3-[3-(3-hydroxypropyl)pyridinium]methyl-3-cephem-4-carboxylate

The preparation was carried out analogously to Example 1.

$^1$H-NMR (D$_2$O) δ (ppm)=8.73 (1H, s, H-2-Py); 8.69 (1H, d, J=7 Hz, H-6-Py); 8.37 (1H, d, J=8 Hz, H-4-Py); 7.92 (1H, dd, J=8 Hz, J=7 Hz, H-5-Py); 5.53 (1H, d, J=14 Hz, CH$_2$-Py); 5.24 (1H, d, J=5 Hz, H-7-lactam); 5.13 (1H, d, J=5 Hz, H-6-lactam); 5.08 (3H, m, Py-CH$_2$—, S—CH$_2$); 3.26 (1H, d, J=18 Hz, S—CH$_2$); 2.85 (2H, t, J=7 Hz, —CH$_2$—OH); and 1.86 (2H, m, —CH$_2$—).

EXAMPLE 46

7-[1-(2-Aminothiazol-4-yl)-1(Z)-propenecarboxamido]-3-[3-(3-hydroxypropyl)pyridinium]methyl-3-cephem-4-carboxylate The preparation was carried out analogously to Example 15

$^1$H-NMR (D$_6$-DMSO) δ (ppm)=9.35 (1H, d, J=7 Hz, H-6-Py 9.23 (1H, s, H-2-Py); 9.11 (1H, d, J=9 Hz, NH); 8.40 (1H, d, J=8 Hz, H-4-Py); 8.02 (1H, dd, J=8 Hz, J=7 Hz, H-5-Py); 6.92 (2H, bs, NH$_2$); 6.24 (1H, q, J=8 Hz, C=C—H); 6.13 (1H, s, thiazole); 5.60 (2H, m, H-7-lactam, CH$_2$-Py); 5.05 (1H, d, J=5 Hz, H-6-lactam; 5.02 (1H, d, J=14 Hz, CH$_2$-Py); 3.50 (1H, d, J=18 Hz, S—CH$_2$); 3.42 (2H, m, Py-CHPy-CH$_2$); 3.05 (1H, d, J=1Hz, S—CH$_2$); 2.80 (2H, m, CH$_2$OH); 1.78 (2H, m, —CH$_2$—); and 1.73 (3H, d, J=8 Hz, C=C—CH$_3$).

EXAMPLE 47

7-Amino-3-[4-(2-hydroxyethyl)pyridinium]methyl-3-cephem-4-carboxylate

The preparation was carried out analogously to Example 1.

$^1$H-NMR (D$_2$O) δ (ppm)=8.75 (2H, d, J=7 Hz, H-2,6 Py); 7.91 (2H, d, J=7 Hz, H-3,5-Py); 5.54 (1H, d, J=14 Hz, CH$_2$-Py); 5.27 (1H, d, J=14 Hz, CH$_2$-Py); 5.25 (1H, d, J=5 Hz, H-7-lactam); 5.14 (1H, d, J=5 Hz, H-6-lactam); 3.88 (2H, t, J=6 Hz, Py-CH$_2$); 3.62 (1H, d, J=18 Hz, S—CH$_2$); 3.27 (1H, d, J=18 Hz, S—CH$_2$); and 3.08 (2H, t, J=6 Hz, CH$_2$—OH).

EXAMPLE 48

7-[1-(2-Aminothiazol-4-yl)-1(Z)-propenecarboxamido]-3-[4(2-hydroxyethyl)pyridinium]methyl-3-cephem-4-carboxylate The preparation was carried out analogously to Example 15.

$^1$H-NMR (D$_6$-DMSO) δ (ppm)=9.35 (2H, d, J=6 Hz, H-2,6Py); 9.21 (1H, d, J=9 Hz, NH); 8.05 (2H, d, J=6 Hz, H-3,5Py); 7.00 (2H, bs, NH$_2$); 6.30 (1H, q, J=8 Hz, C=C—H); 6.18 (1H, s, thiazole); 6.69 (1H, dd, J=9 Hz, J=5 Hz, H-7-lactam); 6.62 (1H, d, J=13 Hz, CH$_2$-Py); 5.12 (1H, d, J=5 Hz, H-6-lactam); 5.08 (1H, d, J=13 Hz, CH$_2$-Py); 3.77 (2H, z, J=6 Hz, Py-CH$_2$); 3.56 (1H, d, J=18 Hz, S—CH$_2$); 3.05 (1H, d, J=18 Hz, S—CH$_2$); 3.02 (2H, m, CH$_2$—OH); and 1.75 (3H, d, J=8 Hz, C=C—CH$_3$).

EXAMPLE 49

7-[1-(2-Aminothiazol-4-yl)-1(Z)-propenecarboxamido]-3-[2(2-hydroxyethyl)pyridinium]methyl-3-cephem-4-carboxylate The preparation was carried out analosously to Example 15.

$^1$H-NMR (D$_6$-DMSO) δ (ppm)=9.45 (1H, d, J7 Hz, H-6-Py); 9.21 (1H, d, J=9 Hz, NH); 8.47 (1H, m, H-4-Py); 02 (2H, m, H-3,5 Py); 6.9 (2H, bs, NH$_2$); 6.29 (1H, q, J=8 Hz, C=C—H); 6.17 (1H, s, thiazole); 5.67 (1H, dd, J=9 Hz, J=5 Hz, H-7-lactam); 5.50 (2H, m, CH$_2$-Py); 5.07 (1H, d, J=5 Hz, H-6-lactam); 3.81 (2H, t, Py-CH$_2$); 3.45 (1H, d, J=18 Hz, S-CH$_2$); 3.37 (2H, m, CH$_2$—OH); 3.05 (1H, d, J=18 Hz, S-CH$_2$); and 1.74 (3H, d, J=8 Hz, C=C—CH$_3$).

EXAMPLE 50

7-Amino-3-[4-(1-hydroxyethyl)pyridinium]methyl-3-cephem-4-carboxylate

The preparation was carried out analogously to Example 1.

$^1$H-NMR (D$_2$O) δ (ppm)=8.90 (2H, d, J=7 Hz, H-2,6-Py); 8.01 (2H, d, J=7 Hz, H-3,5-Py); 5.57 (1H, d, J=15 Hz, CH$_2$-Py); 5.38 (1H, d, J=15 Hz, CH$_2$-Py); 5.35 (1H, d, J=5 Hz, H-7-lactam); 5.22 (2H, m, CH—CH$_3$, H-6-lactam); 3.72 (1H, d, J=18 Hz, S—CH$_2$); 3.35 (1H, d, J=18 Hz, S—CH$_2$); and 1.52 (3H, d, J=7 Hz, CH—CH$_3$).

EXAMPLE 51

7-[1-(2-Aminothiazol-4-yl)-1(Z)-propenecarboxamido]-3-[4-(1-hydroxyethyl)pyridinium]methyl-3-cephem-4-carboxylate The preparation was carried out analogously to Example 15.

$^1$H-NMR (D$_6$O) δ (ppm)=9.41 (2H, d, J=7 Hz, H-2,6-Py); 9.21 (1H, d, J=9 Hz, NH); 8.12 (2H, d, J=7 Hz, H-3,5-Py); 7.01 (2H, bs, NH$_2$); 6.32 (1H, q, J=8 Hz, C=C—H); 6.21 (1H, s, thiazole); 5.68 (2H, m, H-7-lactam, CH$_2$-Py); 5.13 (1H, d, J=5 Hz, H-6-lactam); 5.04 (2H, m, CH$_2$-P , CH—CH$_3$); 3.56 (1H, d, J=18Hz, S-CH$_2$); 3.08 (1H, d, J=18 Hz, S-CH$_2$); 1.77 (3H, d, J=8 Hz, C=C—CH$_3$); and 1.42 (3H, d, J=7 Hz, CH—CH$_3$).

EXAMPLE 52

7-[1-(2-Aminothiazol-4-yl)-1(Z)-propenecarboxamido]-3-[2-(2-propyl-1,3-diol)pyridinium]methyl-3-cephem-4-carboxylate The preparation was carried out analogously to Example 15.

$^1$H-NMR (D$_6$-DMSO) δ (ppm)=9.54 (1H, d, J=7 Hz, H-6-Py); 9.25 (1H, d, J=9 Hz, NH); 8.55 (1H, m, H-4-Py); 8.19 (1H, d, J=7 Hz, H-3-Py); 8.06 (1H, m, H-5-Py); 7.02 (2H, bs, NH$_2$); 6.32 (1H, q, J=8 Hz, C=C—H); 6.21 (1H, s, thiazole); 5.70 (2H, m, H-7-lactam, CH$_2$-Py); 5.52 (1H, d, J=14 Hz, CH$_2$-Py); 5.11 (1H, d, J=5 Hz, H-6-lactam); 4.02 (1H, m, Py-CH; 3.80 (2H, m, CH$_2$—OH); 3.72 (2H, m, CH$_2$—OH); 3.45 (1H, d, J=18 Hz, S—CH$_2$); 3.02 (1H, d, J=18 Hz, S—CH$_2$); and 1.77 (3H, d, J=8 Hz, C=C—CH$_3$).

EXAMPLE 53

7-Amino-3-(6-hydroxymethylquinolinium)methyl-3-cephem-4-carboxylate

The preparation was carried out analogously to Example 1.

$^1$H-NMR (D$_2$O) δ (ppm)=9.23 (1H, d, J=7 Hz, H-2-quin.); 9.16 (1H, d, J=8 Hz, quin.); 8.42 (1H, d, J=8 Hz, quin.); 8.31 (1H, s. quin.); 8.18 (1H, d, J=8 Hz, quin.); 8.06 (1H, dd, J=7 Hz, J=8 Hz, quin.); 6.03 (1H, d, J=15 Hz, CH$_2$-quin.); 5.89 (1H, d, J=15 Hz, CH$_2$-quin.); 5.24 (1H, d, J=5 Hz, H-7-lactam); 5.17 (1H, d, J=5 Hz, H-6lactam); 4.91 (2H, s, CH$_2$—OH); 3.45 (1H, d, J=18 Hz, S—CH$_2$); and 3.27 (1H, d, J=18 Hz, S—CH$_2$).

EXAMPLE 54

7-[1-(2-Aminothiazol-4-yl)-1(Z)-propenecarboxamido]-3-(6-hydroxymethylquinolinium)methyl-3-cephem-4-carboxylate $^1$H-NMR (D$_6$-DMSO) δ (ppm)=9.73 (1H, d, J=7 Hz, H-2quin.); 9.34 (1H, d, J=8 Hz, quin.); 9.26 (1H, J=8 Hz, quin.); 9.13 (1H, d, J=9 Hz, NH); 8.42 (1H, s, quin.); 25 (1H, dd, J=7 Hz, J=Hz, quin.); 8.18 (1H, d, J=8 Hz, quin.); 7.03 (2H, bs, NH$_2$); 6.34 (1H, q, J=8 Hz, C=CH); 6.22 (1H, s, thiazole); 6.08 (1H, d, J=15 Hz, CH$_2$-quin.) 5.96 (1H, d, J=15 Hz, CH$_2$-quin.); 5.71 (1H, dd, J=9 Hz, J=5 Hz, H-7-lactam); 5.11 (1H, d, J=5 Hz, H-6-lactam); 4.86 (2H, s, -CH$_2$OH); 3.42 (1H, d, J=1Hz, S—CH$_2$); 3.01 (1H, d, J=18 Hz, S—CH$_2$); and 1.78 (3H, d, J=Hz, C=C—CH$_3$).

The preparation was carried out analogously to Example 15.

EXAMPLE 55

7-Amino-3-(3-formamidopyridinium)methyl-3-cephem-4-carboxylate $^1$H-NMR (D$_2$O)δ (ppm)=9.53 (1H, s, CHO); 8.70 (1H, d, J=7 Hz, H-6-Py); 8.43 (2H, m, H-2,4-Py); 8.01 (1H, dd, J=8 Hz, J=7 Hz, H-5-Py); 5.65 (1H, d, J=14 Hz, CH$_2$-Py); 5.35 (1H, d, J=14 Hz, CH$_2$-Py); 5.30 (1H, d, J=5 Hz, H-7lactam); 5.19 (1H, d, J=5 Hz, H-6-lactam); 3.71 (1H, d, J=18 Hz, S—CH$_2$); and 3.34 (1H, d, J=18 Hz, S—CH$_2$).

EXAMPLE 56

7-[1-(2-Aminothiazol-4-yl)-1(Z)-propenecarboxamido]-3-(3-formamidopyridinium)methyl-3-cephem-4-carboxylate The preparation was carried out analogously to Example 15.

$^1$H-NMR (D$_6$-DMSO) δ (ppm)=9.68 (1H, s, CHO); 9.25 (2H, m, NH, H-6-Py); 8.7 (1H, d, J=8 Hz, H-4-Py); 8.56 (1H, s, H-2-Py); 8.13 (1H, m, H-5-Py); 7.01 (2H, bs, NH$_2$); 6.32 (1H, q, J=8 Hz, C=C—N); 6.20 (1H, s, thiazole); 5.72 (2H, m, CH$_2$-Py, H-7-lactam); 5.25 (1H, d, J=14 Hz, CH$_2$—Py); 5.13 (1H, d, J=5 Hz, H-6-lactam); 3.57 (1H, d, J=18 Hz, S—CH$_2$); 3.16 (1H, d, J=18 Hz, S—CH$_2$); and 1.76 (3H, d, J=8 Hz, C=C—CH$_3$).

EXAMPLE 57

7-[1-(2-Aminothiazol-4-yl)-1(Z)-propenecarboxamido]-3-(3-aminopyridinium)methyl-3-cephem-4-carboxylate A solution of 500 mg of 7-[1-(2-aminothiazol-4 -yl)-1(Z)-propenecarboxamido]-3-(3-for-mylamidopyridinium) -methyl-3-cephem-4-carboxylate in 6 ml of methanol and 0.3 ml of concentrated hydrochloric acid is stirred at room temperature for 5 hours. The solvent is stripped off in vacuo, the residue is taken up in a little water and the mixture is neutralized with ion exchanger MP 62 and purified over adsorber resin HP 20 (elution with water and increasing amounts of acetonitrile). Yield: 240 mg.

$^1$H-NMR (D$_6$-DMSO) (ppm)=9.20 (1H, d, J=9 Hz, NH); 58 (1H, s, H-2-Py); 8.46 (1H, d, J=7 Hz, H-6-Py); 7.71 (1H, dd, J=7 Hz, H=Hz, H-5-Py); 7.57 (1H, d, J=8 Hz, H-4-Py); 7.01 (2H, bs, NH$_2$); 6.73 (2H, bs, NH$_2$); 6.31 (1H, q, J=8 Hz, C=C—H); 6.19 (1H, s, thiazole); 5.67 (1H, dd, J=9 Hz, J=5 Hz, H-7-lactam); 5.59 (1H, d, J=14 Hz, CH$_2$-Py); 5.08 (1H, d, J=5 Hz, H-6-lactam); 4.95 (1H, d, J=14 Hz, CH₂—Py); 4.48 (1H, d, J=18 Hz, S—CH₂); 3.00 (1H, d, J=18 Hz, S—CH₂); and 1.76 (3H, d, J=8 Hz, C═C—CH₃).

It will be understood that the specification and examples are illustrative but not limitative of the present invention and that other embodiments within the spirit and scope of the invention will suggest themselves to those skilled in the art.

We claim:

1. A compound of the formula

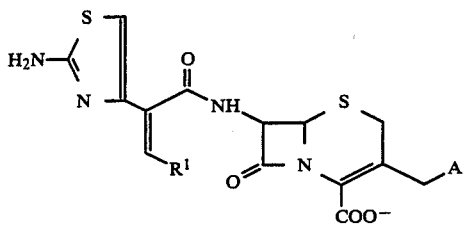

in which
R₁ represents C₁-C₅-alkyl, and
A is a pyridinium radical which is substituted by hydroxy-C₁-C₄-alkyl, carboxy C₁-C₄-alkyl, C₁-C₄-alkoxycarbonyl -C₁-C₄-alkyl, formyl-C₁-C₄-alkyl, C₁-C₄-alkylcarbonyl-groups of which can also additionally be substituted by hydroxyl and the carbonyl group of which can also be in ketalized form, carbamoylsubstituted C₁-C₄-alkyl, which can also be further substituted on the nitrogen by hydroxyl, sulpho-C₁-C₄-alkyl, 1-hydroxy-1-sulphomethyl, C₁-C₄-alkoxy-C₁-C₄-alkyl, which can also be substituted by hydroxyl, C₁-C₄-alkylthio-C₁-C₄-alkyl, C₁-C₄-alkylsulphinyl-C₁-C₄-alkyl, C₁-C₄-alkylsulphonyl-C₁-C₄-alkyl, C₃-alkenyloxy-C₁-C₄-alkyl, C₃-alkenylthio-C₁-C₄-alkyl, C₃-alkenylsulphinyl-C₁-C₄-alkyl, C₃-alkenylsulphonyl-C₁-C₄-alkyl, cyano-C₁-C₃-alkyl, epoxy-C₂-C₃-alkyl, trifluoromethyl, hydroximinomethyl, C₁-C₃-alkyloxyiminomethyl, C₃-C₄-alkenyl, which can also be substituted by hydroxyl, C₃-alkinyl, C₃-C₆-cycloalkyl, and C₃-C₆-cycloalkyl-methyl, it being possible for the ring also to be substituted by hydroxyl, by halogen, or by carboxyl, C₁-C₄-alkoxycarbonyl, cyano, C₅-C₆-cycloalkenyl, C₁-C₄-alkoxy, it being possible for these alkoxy groups to be additionally substituted by hydroxyl, carboxyl or C₁-C₄-alkoxycarbonyl, epoxy-C₂-C₃alkoxy, C₃-alkenyloxy, C₃-alkinyloxy, aryloxy, amino, C₁-C₅-alkylamino, C₁-C₄-dialkylamino, C₁-C₄-alkoxycarbonylamino, C₁-C₄-alkylcarbonylamino, N-C₁-C₄-alkyl- and dialkylcarbamoylamino, C₁-C₄-alkylsulphonylamino, hydroxyl, C₁-C₄-alkylthio, which can also be substituted by hydroxyl, C₁-C₄-alkylsulphinyl, which can also be substituted by hydroxyl, C₁-C₄-alkylsulphonyl, which can also be substituted by hydroxyl, carboxymethylthio and C₁-C₄-alkoxycarbonylmethylthio, and C₁-C₄-alkoxycarbonymethyl-sulphinyl and -sulphonyl, C₃-alkenylthio, C₃-alkenylsulphinyl, C₃-alkenylsulphonyl, phenyl and benzyl, which can also be, substituted by halogen, 2'-thienyl and 3'thienyl, formyl and ketalized formyl, C₁-C₄-alkylcarbonyl, which can also be substituted by hydroxyl and can be in ketalized form, benzoyl, C₁-C₄-alkylcarbonylamino, formylamino, carboxyl, and C₁-C₄-alkoxycarbonyl, and onto which an optionally substituted 5-membered or 6-membered ring can be fused, which can contain up to two hetero-atoms and up to two double bonds, or a pharmaceutically acceptable salt thereof or ester thereof which can be split under physiological conditions.

2. A compound, salt or ester according to claim 1, in which there is a fused-on ring chosen from the group comprising cyclopenteno, dehydrocyclopenteno, cyclohexeno, dehydrocyclohexeno, benzo, furo, dihydrofuro, pyrano, dihydropyrano, thieno, dihydrothieno, thiopyrano, dihydrothiopyrano, pyrido, dihydropyrido, tetrahydropyrido, pyrimido, dihydropyrimido, tetrahydropyrimido, pyrazino, dihydropyranizo, tetrahydropyrazino pyridazino, dihydropyridazino and tetrahydropyridazino, each of which can be substituted by C₁-C₄-alkyl, C₃-C₆-cycloalkyl, C₁-C₄-alkoxy, C₁-C₃-hydroxyalkyl, halogen, hydroxyl, carboxyl, cyano C₁-C₆-alkoxycarbonyl, oxo, hydroximino, carbamoyl, sulphamoyl, amino, C₁-C₄-alkylamino, and C₁-C₄-dialkylamino.

3. A compound according to claim 1, wherein such compound is 7-[1-(2-aminothiazol-4-yl)-1(Z)-propenecarboxamido]-3-(4-hydroxymethylpyridinium)-methyl-3- cephem-4-carboxylate of the formula

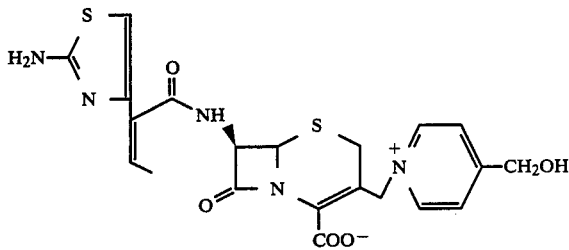

or a pharmaceutically acceptable salt thereof or ester thereof which can be split under physiological conditions.

4. A compound according to claim 1, wherein such compound is 7-[1-(2-aminothiazol-4-yl)-1(Z)-propenecarboxamido]-3-(2-hydroxymethylpyridinium)-methyl-3- cephem-4-carboxylate of the formula

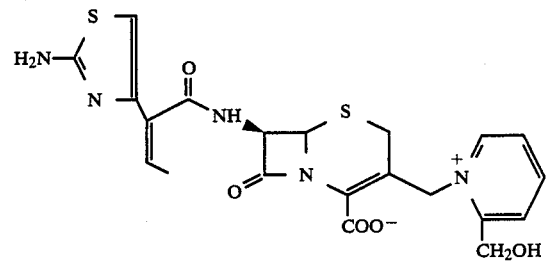

or pharmaceutically acceptable salt thereof of ester thereof which can be split under physiological conditions.

5. A compound according to claim 1, wherein such compound is 7-[1-(2-aminothiazol-4-yl)-1(Z)-propenecarboxamido]-3-(4-cyclopropylpyridinium)-methyl-3-cephem-4-carboxylate of the formula

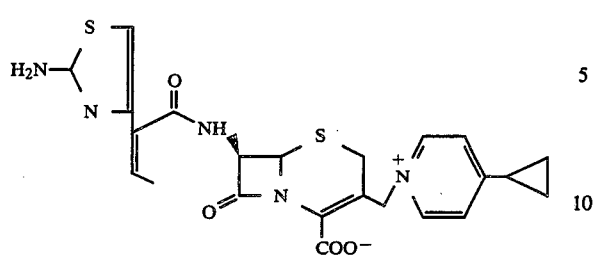

or a pharmaceutically acceptable salt thereof or ester thereof which can be split under physiological conditions.

6. A compound according to claim 1, wherein such compound is 7-[1-(2-aminothiazol-4-yl)-1(Z)-propenecarboxamido]-3-isoquinoliniummethyl-3-cephem-4-carboxylate of the formula

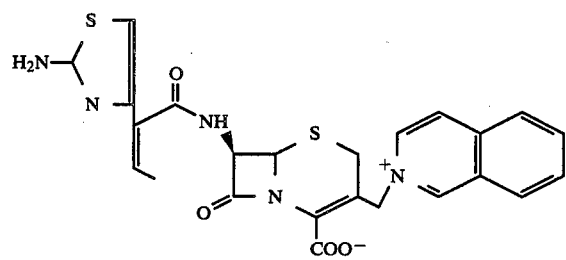

or a pharmaceutically acceptable salt thereof or ester thereof which can be split under physiological conditions.

7. A compound according to claim 1, wherein such compound is 7-[1-(2-aminothiazol-4-yl)-1(Z)-propenecarboxamido]-3-(3-aminopyridinium)methyl-3-cephem-4-carboxylate of the formula

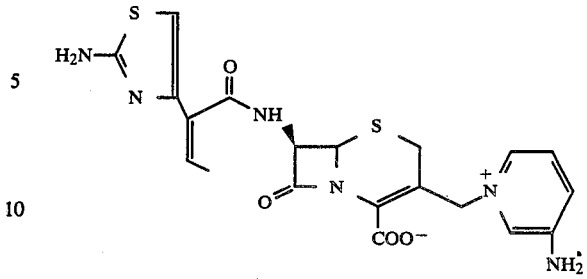

or a pharmaceutically acceptable salt thereof or ester thereof which can be split under physiological conditions.

8. An antibacterial composition comprising an antibacterially effective amount of a compound, salt or ester according to claim 1 in admixture with a diluent.

9. A unit dose of a composition according to claim 1 in the form of a tablet, capsule or ampule.

10. A method of combating bacteria which comprises administering to a patient an antibacterially effective amount of a compound, salt or ester according to claim 1.

11. The method according to claim 10, wherein such compound is
7-[1-(2-aminothiazol-4-yl)-1(Z)-propenecarboxamido]-3-(4-hydroxymethylpyridinium)methyl-3-cephem-4-carboxylate,
7-[1-2-aminothiazol-4-yl)-1(Z)-propenecarboxamido]-3-(2-hydroxymethylpyridinium)methyl-3-cephem-4-carboxylate,
7-[1-(2-aminothiazol-4-yl)-1(Z)-propenecarboxamido]-3-(4-cyclopropylpyridinium)methyl-3-cephem-4-carboxylate,
7-[1-(2-aminothiazol-4-yl)-1(Z)-propenecarboxamido]-3-isoquinoliniummethyl-3-cephem-4-carboxylate or
7-[1-(2-aminothiazol-4-yl)-1(Z)-propenecarboxamido]-3-(3-aminopyridinium)methyl-3-cephem-4-carboxylate,
or a pharmaceutically acceptable salt thereof or ester thereof which can be split under physiological conditions.

* * * * *

UNITED STATES PATENT AND TRADEMARK OFFICE
CERTIFICATE OF CORRECTION

PATENT NO. : 4,757,065

DATED : Jul. 12, 1988

INVENTOR(S) : Angerbauer et al.

It is certified that error appears in the above-identified patent and that said Letters Patent is hereby corrected as shown below:

| | |
|---|---|
| Col. 2, line 40 | Insert -- - -- before "alkylthio" |
| Col. 4, line 9 | Insert -- - -- after "1" in third instance |
| Col. 4, line 60 | Insert -- - -- after "methyl" |
| Col. 6, line 47 | Delete "$\equiv$" after "$R^2$" and insert -- = -- |
| Col. 10, line 64 | Correct spelling of --especially-- |
| Col. 14, line 7 | Delete "noncoccus" and substitute --non-- |
| Col. 14, line 18 | Delete "P-r." and substitute --Pr.-- |
| Col. 17, line 12 | Insert -- - -- after "7" |
| Col. 18, line 41 | Insert -- - -- after "H-6" |
| Col. 19, line 34 | Correct spelling of --dimethylformamide-- |
| Col. 19, line 46 | Insert -- 7- -- before "lactam" |
| Col. 20, line 17 | Insert --2-- after "S-CH" in second instance |
| Col. 20, line 22 | Delete "1" after "pyridinium" and insert --]-- |
| Col. 20, line 39 | Correct spelling of --propenecarboxamido-- and insert --]-- after such word |
| Col. 21, line 31 | Insert -- - -- after "H-6" |
| Col. 22, line 38 | Delete "carb" and substitute --carboxylate-- |
| Col. 22, line 44 | Delete "04" and insert --8.04-- |
| Col. 22, line 54 | Correct spelling of --carboxylate-- |
| Col. 23, line 62 | Correct spelling of --propenecarboxamido-- |
| Col. 23, line 67 | Delete "6.3" and insert --6.38-- |
| Col. 24, line 4 | Delete "1Hz" and insert --18 Hz-- |
| Col. 24, line 65 | Delete "77" and insert --8.77-- |
| Col. 26, line 16 | Delete "CHPy" |
| Col. 26, line 17 | Delete "1Hz" and insert --18 Hz-- |

UNITED STATES PATENT AND TRADEMARK OFFICE
CERTIFICATE OF CORRECTION

PATENT NO. : 4,757,065
DATED : Jul. 12, 1988
INVENTOR(S) : Angerbauer et al.

It is certified that error appears in the above-identified patent and that said Letters Patent is hereby corrected as shown below:

| | |
|---|---|
| Col. 26, line 57 | Correct spelling of --analogously-- |
| Col. 26, line 59 | Delete "J7" and insert --J=7-- |
| Col. 26, line 61 | Delete ".02" and insert --8.02-- |
| Col. 27, line 24 | Delete "($D_6$O)" and insert --($D_6$-DMSO)-- |
| Col. 27, line 48 | Delete "3.80" and insert --3.84-- |
| Col. 28, line 9 | Delete "25" and insert --8.25-- |
| Col. 28, line 9 | Delete "J=Hz" and insert --J=8 Hz-- |
| Col. 28, line 16 | Delete "1Hz" and insert --J=18 Hz-- |
| Col. 28, line 17 | Delete "J=Hz" and insert --J=8 Hz-- |
| Col. 28, line 64 | Delete "H=Hz" and insert --H=8 Hz-- |
| Col. 29, line 27 | Insert --$C_1$-$C_4$-alkyl, the two alkyl-- before "groups" |

Signed and Sealed this

Seventh Day of March, 1989

Attest:

DONALD J. QUIGG

Attesting Officer

Commissioner of Patents and Trademarks